United States Patent
Mousa et al.

(10) Patent No.: US 9,956,181 B2
(45) Date of Patent: May 1, 2018

(54) COMPOSITION OF NANOFORMULATED LYCOPENE AND METHOD OF USING THE COMPOSITION

(71) Applicants: Shaker A. Mousa, Wynantskill, NY (US); Mohammed H. Qari, Jeddah (SA); Mohammed-Salleh M. Ardawi, Jeddah (SA)

(72) Inventors: Shaker A. Mousa, Wynantskill, NY (US); Mohammed H. Qari, Jeddah (SA); Mohammed-Salleh M. Ardawi, Jeddah (SA)

( * ) Notice: Subject to any disclaimer, the term of this patent is extended or adjusted under 35 U.S.C. 154(b) by 0 days. days.

(21) Appl. No.: 15/260,967

(22) Filed: Sep. 9, 2016

(65) Prior Publication Data
US 2017/0071873 A1    Mar. 16, 2017

Related U.S. Application Data

(60) Provisional application No. 62/217,167, filed on Sep. 11, 2015.

(51) Int. Cl.
| | | |
|---|---|---|
| A61K 9/50 | (2006.01) |
| A61K 31/01 | (2006.01) |
| A61K 9/19 | (2006.01) |
| A61K 9/51 | (2006.01) |
| A61K 9/16 | (2006.01) |
| A61K 31/353 | (2006.01) |
| A61K 47/59 | (2017.01) |
| A61K 47/69 | (2017.01) |

(52) U.S. Cl.
CPC ............ *A61K 31/01* (2013.01); *A61K 9/1652* (2013.01); *A61K 9/19* (2013.01); *A61K 9/5031* (2013.01); *A61K 9/5036* (2013.01); *A61K 9/5123* (2013.01); *A61K 9/5146* (2013.01); *A61K 9/5161* (2013.01); *A61K 31/353* (2013.01); *A61K 47/59* (2017.08); *A61K 47/6925* (2017.08); *A61K 9/5153* (2013.01)

(58) Field of Classification Search
CPC ........................... A61K 9/5036; A61K 9/1652
See application file for complete search history.

(56) References Cited

PUBLICATIONS

Lei et al, "Impact of Chitosan-EGCG conjuates on Physicochemical Stability of Beta-Carotene Emulsion", Foof Hydrocolloids, 2014.*

* cited by examiner

*Primary Examiner* — Carlos A Azpuru
(74) *Attorney, Agent, or Firm* — Schmeiser, Olsen & Watts, LLP

(57) ABSTRACT

A nano-composition and a method of using the composition. The composition includes nanoparticles. Each nanoparticle includes a shell encapsulating lycopene. The shell includes oligomerized (−)-epigallocatechin-3-O-gallate (OEGCG) electrostatically bonded to chitosan. The method of using the composition includes administering the nano-composition to a human being.

15 Claims, 10 Drawing Sheets

US 9,956,181 B2

COMPOSITION OF NANOFORMULATED LYCOPENE AND METHOD OF USING THE COMPOSITION

RELATED APPLICATION

The present invention claims priority to U.S. Provisional No. 62/217,167 filed on Sep. 11, 2015, which is incorporated herein by reference in its entirety.

FIELD OF THE INVENTION

The present invention relates to a composition of Nano-formulated lycopene with other bioactive anti-oxidants and methods of using the composition for bone health, body weight loss, and other organ protective utilities.

BACKGROUND OF THE INVENTION

Postmenopausal osteoporosis is a serious public health concern associated with significant morbidity, mortality, deterioration of quality of life, and high health care costs (Kanis J A. Assessment of fracture risk and its application to screening for postmenopausal osteoporosis: synopsis of a WHO report, WHO Study Group. Osteoporosis Int. 1994; 4:368-8).

Current FDA-approved therapies include anti-resorptive (e.g., bisphosphonate and denosumab) and anabolic (e.g., teriparatide) agents (America's bone health: the state of osteoporosis and low bone mass in our nation, NOF 2002 [NOF 2002]).

While denosumab is relatively new and unstudied, bisphosphonate and teriparatide therapies have contributed to a documented decrease in fracture risk among treated patients (Freemantle N, Cooper C, Diez-Perez A, Gitlin M, Radcliffe H, Shepherd S, et al, Results of indirect and mixed treatment comparison of fracture efficacy for osteoporosis treatments: a meta-analysis, Osteoporosis Int. 2013; 24:209-17).

However, the potentially undesirable side effects associated with these pharmacological therapies, including atypical fractures, osteonecrosis of the jaw, gastro-oesophageal adverse events, and dizziness, along with poor compliance and cost concerns for teriparatide, continue to challenge their overall efficacy [4, 5] (Stroup J, Kane M P, Abu-Baker A M, Teriparatide in the treatment of osteoporosis, Am J Health Syst Pharm 2008; 65:532-9); (Curtis J R, Cai Q, Wade S W, Stolshek B S, Adams J L, Balasubramanian A, et al., Osteoporosis medication adherence: physician perceptions vs patients utilization, Bone 2013; 55:1-6.).

Thus, research efforts are directed towards discovering more effective, lower-cost therapeutic strategies, including natural alternatives with minimal side effects and fewer compliance challenges.

There is growing evidence that oxidative stress, induced by reactive oxygen species (ROS) that increase with aging or with the onset of an inflammatory state, can adversely affect bone homeostasis (Callaway D A, Jiang J X, Reactive oxygen species and oxidative stress in osteoclastogenesis, skeletal aging and bone disease, J Bone Miner Metab 2015; DOI 10.1007/s00774-015-0656-4).

Recent studies have suggested that postmenopausal bone loss may be caused by ROS, which induce a more oxidized bone microenvironment (Maggio D, Barabani M, Pierandrei M, Polidori M C, Catani M, Mecocci P, et al., Marked decrease in plasma antioxidants in aged osteoporotic women: Results of a cross-sectional study, J Clint Endocrinol Metab 2003; 88:1523-7).

An excess of ROS may inhibit osteoblast differentiation and proliferation (Li M, Zhao L, Liu A L, Zeng W S, Luo S Q, et al., Hydrogen peroxide induces G2 cell cycle arrest and inhibit cell proliferation in osteoblast, Anat Res 2009; 292: 1107-13).

ROS generated in the extra- or intra-osteoclasts act as signals to enhance osteoclastic differentiation, resulting in more bone resorption (Fraser J H E, Halfrich M H, Wallace W M, Ralston S H., Hydrogen peroxide, but not superoxide, stimulates bone resorption in mouse calvaria, Bone 1996; 19:223-6); (Lee N K, Choi Y G, Baik J Y, Han S Y, Jeong Bae Y S, et al., A crucial role for reactive oxygen species in RANKL-induced osteoclast differentiation, Blood 2005; 106:852-9).

Thus, an imbalance in ROS levels can accelerate bone resorption, resulting in bone fragility and fracture: accordingly, eliminating excessive ROS is an effective approach for maintaining bone integrity (Banifi G, Iorio E L, Corsi M M., Oxidative stress, free radical and bone remodeling, Clin Chem Lab Med 2008; 46:1550-5).

Estrogen deficiency, an independent risk factor for bone fragility (Weitzmann M N, Pacifici R., estrogen deficiency and bone loss: an inflammatory state, J Clin Invest 2006; 116:1186-94), has been linked to an increase in oxidative stress.

Dietary supplementation or treatment with antioxidants is an effective approach to counteract and ameliorate excessive ROS production. Lycopene, a carotenoid found in red fruits and vegetables, especially tomatoes and tomato products, is one of the most potent antioxidants but has low oral bioavailability with consequent low efficiency of utilization.

SUMMARY OF THE INVENTION

The present invention provides a nano-composition and a method of using the composition. The nano-composition includes nanoparticles. Each nanoparticle includes a shell encapsulating lycopene. The shell includes oligomerized (−)-epigallocatechin-3-O-gallate (OEGCG) electrostatically bonded to chitosan. The method of using the composition includes administering the nano-composition to a human being.

DETAILED DESCRIPTION OF THE INVENTION

Figure 1:
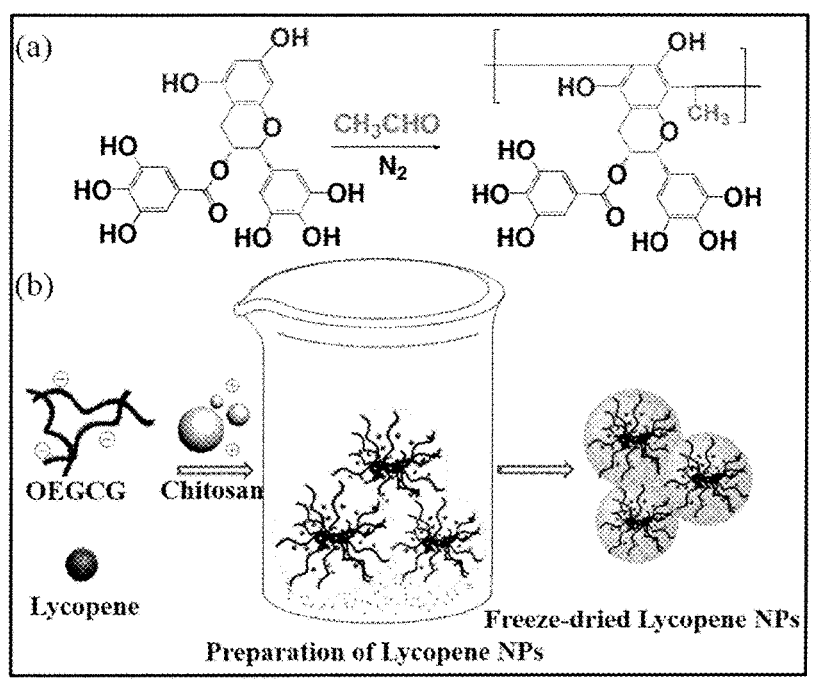
FIG. 1 depicts a nano-lycopene synthesis and formulation, in accordance with embodiments of the present invention.

The preset invention provides a nano-composition comprises nanoparticles. Each nanoparticle comprises a shell encapsulating lycopene, said shell comprising oligomerized (−)-epigallocatechin-3-O-gallate (OEGCG) electrostatically bonded to chitosan.

In one embodiment, the shell is coated with a targeting moiety configured to target the nanoparticle to a liver of a human being to which the nanoparticles are administered. The targeting moiety may be Glycyrrhizin.

In one embodiment, the shell further comprises the chitosan covalently bonded to a carboxyl group of each polymer of one or more polymers. Each polymer of the of one or more polymers may be selected from the group consisting of hyaluronic acid, Poly (Lactide-co-Glycolide) (PLGA), one or more fatty acids, and combinations thereof. The one or more polymers may comprise the hyaluronic acid. The one or more polymers may comprise the PLGA. The one or more polymers may comprise the one or more fatty acids, wherein the one or more fatty acids may be selected from the group consisting of oleic acid, myristic acid, docosahexaenoic acid (DHA), eicosapentaenoic acid (EPA), and combinations thereof.

In one embodiment, the shell further encapsulates one or more bioactive compounds comprising polyphenols.

In one embodiment, the chitosan has a molecular weight in a range of 5,000 to 100,000 Daltons.

In one embodiment, each nanoparticle has a linear size in a range of 100 to 500 nm.

In one embodiment, each nanoparticle has a positive zeta potential in a range of +10 to +30 mv.

The present invention provides a method of forming the nanoparticles in the nano-composition. The method of forming the nanoparticles comprises: mixing lycopene in olive oil with docosahexaenoic acid (DHA) and/or eicosapentaenoic acid (EPA) in a presence of Cremopher EL and Tween 20, wherein the formed nanoparticles are solid lipid nanoparticles. The method of forming the nanoparticles may further comprise: lyophilizing the nanoparticles; and prior to said lyophilizing the nanoparticles, adding mannitol or sucrose as a cryoprotectant to the nanoparticles.

The present invention provides a method of using the nano-composition. The method of using the nano-composition comprises: administering the nano-composition to a human being.

In one embodiment, the human being has osteoporosis, wherein the administered nano-composition combats the osteoporosis in the human being.

In one embodiment, the human being is obese, wherein the administered nano-composition promotes loss of body weight in the human being.

In one embodiment, the human being has an impairment of an organ, wherein the impairment is selected from the group consisting oxidative damage, tissue fibrosis, and a combination thereof, wherein the administered nano-composition combats the impairment. The organ may be selected from the group consisting of liver, kidney, heart, brain, and lung.

In one embodiment, the human being has scleroderma, wherein the administered nano-composition combats the scleroderma.

In one embodiment, administering the nano-composition to the human being comprises administering the nano-composition orally, topically, or by injection.

Lycopene supplementation decreases oxidative stress and exhibits beneficial effects on bone health, but it has poor solubility limiting its oral bioavailability impacting its pharmacokinetic (PK) and pharmacodynamic (PD) properties. A green tea catechin derivative, oligomerized (−)-epigallocatechin-3-O-gallate (OEGCG) was used as a natural carrier for oral lycopene delivery. Lycopene-loaded OEGCG nanoparticles (NPs) was prepared by a nano-precipitation method, followed by coating with chitosan to form a shell. This method not only can easily control the size of the NP to be around 150-250 nm to improve its bioavailability, but can also effectively protect the lycopene against oxidation due to EGCG's anti-oxidant property. OEGCG was characterized with nuclear magnetic resonance spectroscopy and time of flight mass spectrometry. Chitosan-coated OEGCG/lycopene NPs had a diameter of 150-250 nm and a ζ-potential of +30 to +40 mv as characterized with transmission electron microscopy and dynamic light scattering. The loading capacity of lycopene was 10-15% and encapsulation efficiency was 90%. FT-IR spectra analysis revealed electrostatic interaction between OEGCG and chitosan. Additionally, covalent bonding with Chitosan and fatty acid such as hyaluronic acid was achieved in the presence of catalyst such as EDC. Freeze drying of the NPs was also evaluated as a means to improve shelf life. The in vitro release study showed slow release of lycopene in simulated gastric fluid at acidic pH and faster release in simulated intestinal fluid. In an in vivo study in mice, lycopene pharmacokinetic parameters were improved by lycopene/OEGCG/chitosan NPs. The self-assembled nanostructure of OEGCG combined with lycopene demonstrated distinct improvement in oral bioavailability, which lycopene utility in various diseases including osteoporosis, obesity, and organs (kidney, liver, heart, lung, and brain) protection against various insult.

The effects of novel Nanoformulated lycopene treatment on postmenopausal osteoporosis were evaluated. Six-month-old female Wistar rats (n=264) were sham-operated (SHAM) or ovariectomized (OVX). The SHAM group received oral vehicle only and the OVX rats were randomized into five groups receiving oral daily lycopene treatment (mg/kg body weight per day): 0 OVX (control), 15 OVX, 30 OVX, and 45 OVX, and one group receiving alendronate (ALN) (2 µg/kg body weight per day), for 12 weeks. Bone densitometry measurements, bone turnover markers, biomechanical testing, and histomorphometric analysis were conducted. Micro computed tomography was also used to evaluate changes in microarchitecture. Lycopene treatment suppressed the OVX-induced increase in bone turnover, as indicated by changes in biomarkers of bone metabolism: serum osteocalcin (s-OC), serum N-terminal pro-peptide of type I collagen (s-PINP), serum cross-linked carboxyterminal telopeptides (s-CTX-1), and urinary deoxypyridinoline (u-DPD). Significant improvement in OVX-induced loss of bone mass, bone strength, and micro-architectural deterioration was observed in lycopene-treated OVX animals. These effects were observed mainly at sites rich in trabecular bone, with less effect in cortical bone. Lycopene treatment down-regulated osteoclast differentiation concurrent with up-regulating osteoblast together with glutathione peroxidase (GPx) catalase (CAT) and superoxide dismutase (SOD) activities. These findings demonstrate that lycopene treatment in OVX rats primarily suppressed bone turnover to restore bone strength and microarchitecture.

To provide more insight into the possible mechanisms of the bone-sparing effects of lycopene, the effect of lycopene treatment on bone loss in an OVX rat model was investigated. Bone health was comprehensively assessed with measurements of BTMs, bone mass, bone dynamics, bone microarchitecture, and bone strength parameters. Alterations in regulators of oxidative stress and of osteoblast and osteoclast differentiation and activity at the tissue level were evaluated. Additionally, alendronate (ALN) treatment as a positive control to compare the bone metabolic response to lycopene treatment with that of an established anti-resorptive therapy was used.

FIG. 1 depicts a nano-lycopene synthesis and formulation, in accordance with embodiments of the present invention. The nano-lycopene synthesis and formulation includes: (a) Chemical structure and schematic illustration of oligomerized (−)-epigallocatechin-3-O-gallate (OEGCG) synthesized from the intermolecular polycondensation reaction of EGCG; and (b) Schematic of the self-assembly process used to form the lycopene/OEGCG/chitosan nanoparticles (NPs), which are formed via two sequential self-assembly processes in an aqueous solution: complexation of OEGCG with lycopene to form the core, followed by coating with chitosan to form the shell.

Figure 2:
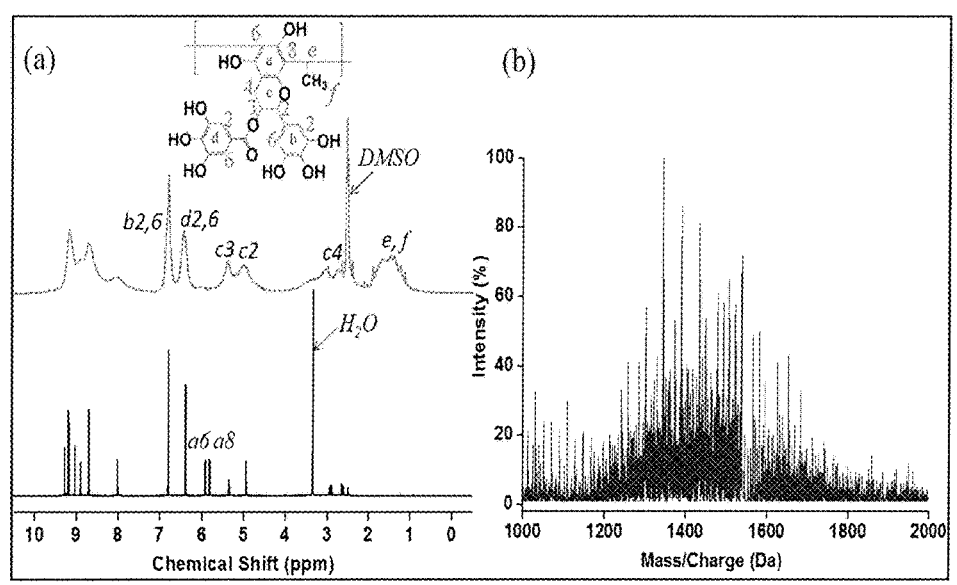
FIG. 2 depicts Nuclear Magnetic Resonance (NMR) spectra, in accordance with embodiments of the present invention.

FIG. 2 depicts Nuclear Magnetic Resonance (NMR) spectra, in accordance with embodiments of the present invention. The NMR spectra include: (a) $^1$H NMR spectra of OEGCG (top, red) and EGCG (bottom, black). Both spectra were recorded in DMSO-$d_6$. The new peak from 1.1 to 1.9 ppm was assigned to the methyl (f) and methine (e) protons of the main chain carbon bridge. (b) MALDI-TOF mass spectrum of OEGCG.

Figure 3:
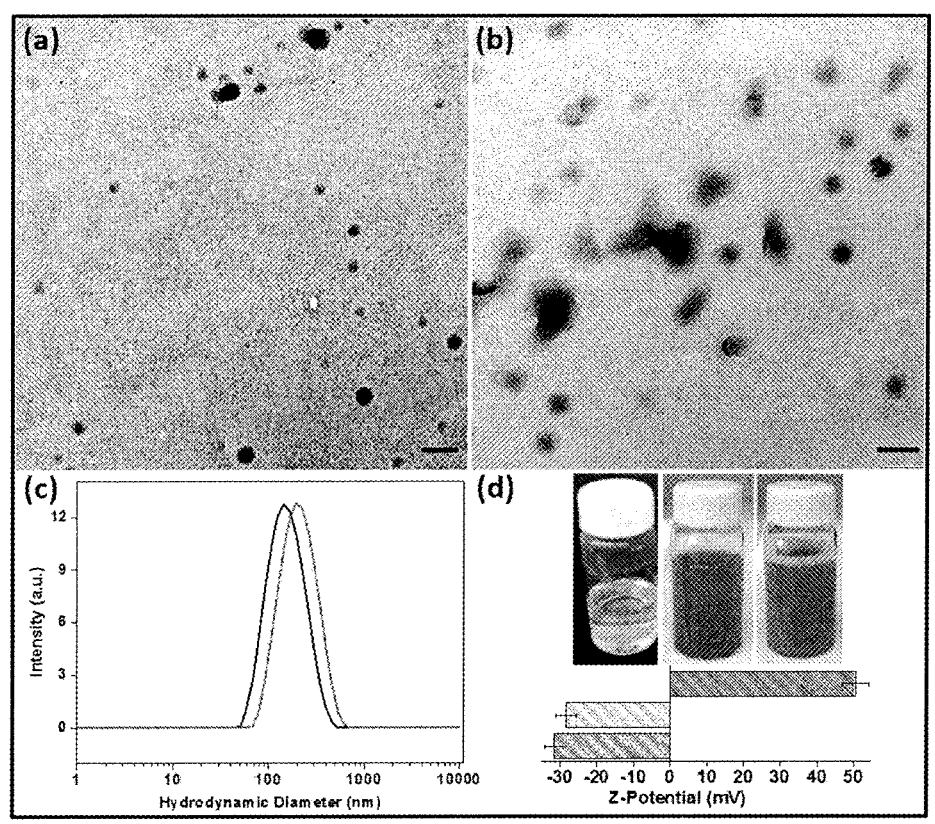
FIG. 3 depicts transmission electron microscopy (TEM) images, in accordance with embodiments of the present invention.

FIG. 3 depicts transmission electron microscopy (TEM) images, in accordance with embodiments of the present invention. The TEM images are of (a) lycopene/OEGCG nanoparticles (NPs); (b) lycopene/OEGCG/chitosan NPs. Scale bars are 200 nm in (a, b). (c) The hydrodynamic diameter of lycopene/OEGCG NPs before (black) and after (red) coating with chitosan, measured with dynamic light scattering (DLS). (d) ζ-potential of OEGCG NPs (red), lycopene/OEGCG NPs before (green) and after (blue) being coated with chitosan in water. Photographs of vials from left to right are the empty OEGCG NPs, lycopene/OEGCG NPs, and lycopene/OEGCG/chitosan NPs dispersed in water.

Figure 4:
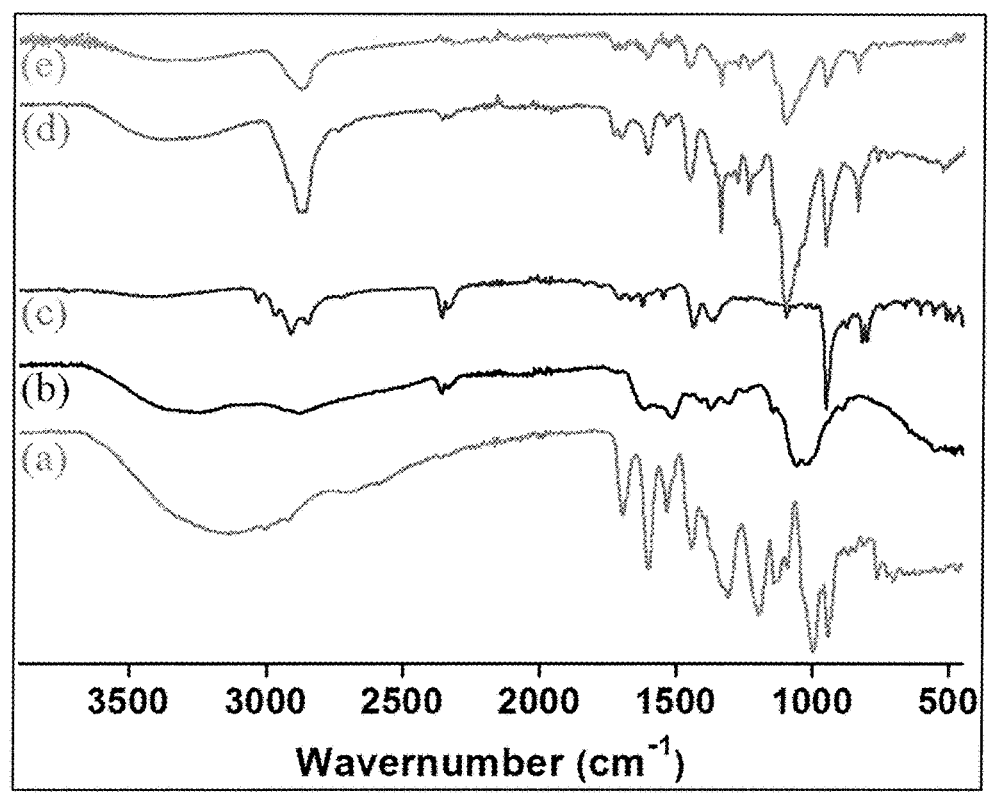
FIG. 4 depicts Fourier Transform infrared (FT_IR) spectra, in accordance with embodiments of the present invention.

FIG. 4 depicts Fourier Transform Infrared (FT_IR) spectra, in accordance with embodiments of the present invention. The FT_IR spectra are of (a) OEGCG, (b) chitosan, (c) lycopene. (d) lycopene/OEGCG nanoparticles (NPs) and (e) lycopene/OEGCG/chitosan NPs. The peak at 3180 cm$^{-1}$ is the O—H stretch and peaks at 1608 cm$^{-1}$ and 1533 cm$^{-1}$ are from the benzene ring C=C stretch in EGCG (a). Peaks for chitosan's amide I and II groups' N—H bend were found at 1618 cm$^{-1}$ and 1506 cm$^{-1}$ in chitosan, respectively (b). The peak at 3043 cm$^{-1}$ represents the unsaturation absorption peak in lycopene (c).

Figure 5:
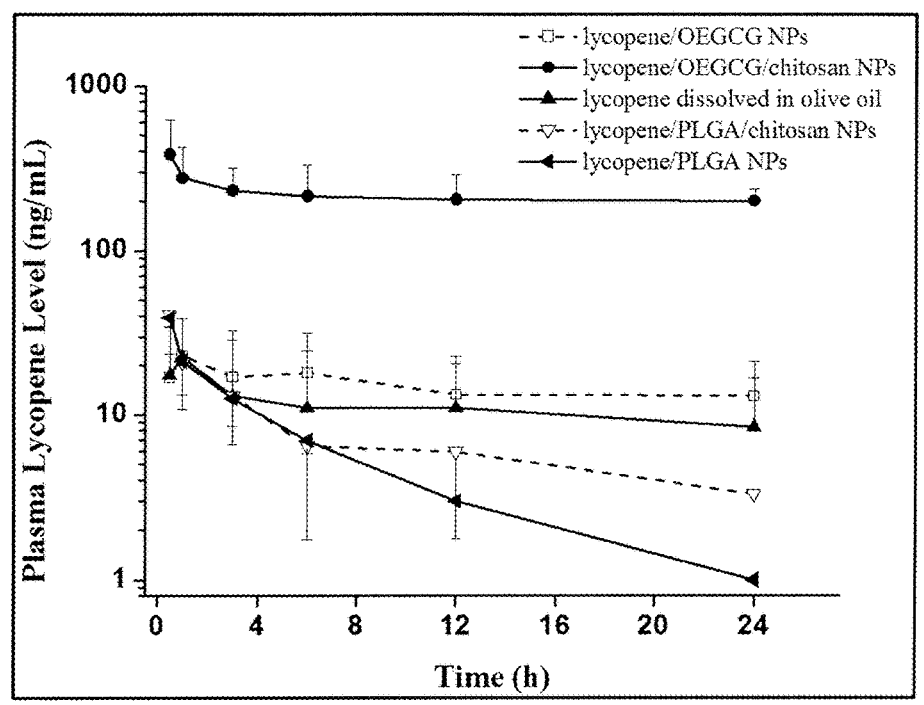
FIG. 5 depicts oral bioavailability of nano lycopene versus lycopene, in accordance with embodiments of the present invention.

FIG. 5 depicts oral bioavailability of nano lycopene versus lycopene, in accordance with embodiments of the present invention. FIG. 5 includes mouse plasma lycopene level versus time profiles. Different formulations: lycopene/OEGCG/chitosan (●, solid line), lycopene/OEGCG (□, dash line), lycopene dissolved in olive oil (▲, solid line), lycopene/PLGA (◀, solid line) and lycopene/PLGA/chitosan (∇, dash line) were administered by oral gavage into mice at a dose of 10 mg/kg body weight. Data are shown as mean±SD (n=4).

Figure 6:
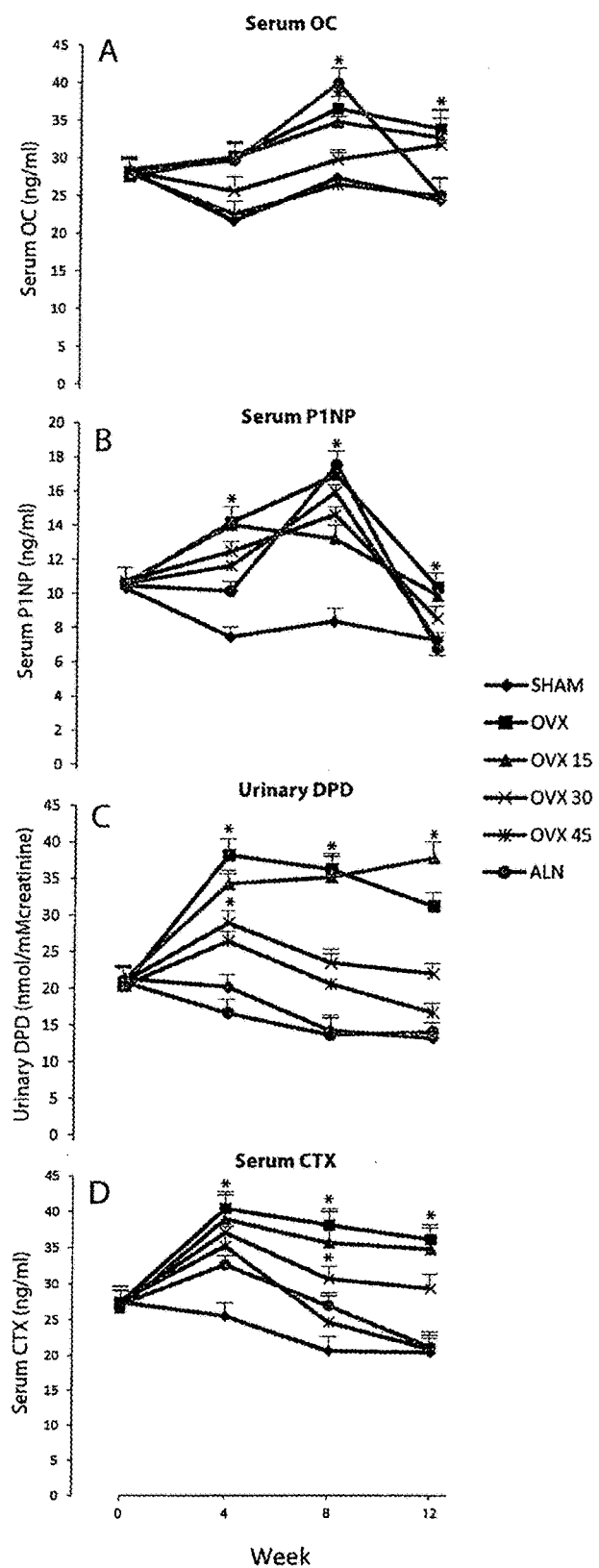
FIG. 6 depicts changes in biochemical bone turnover markers in response to treatment, in accordance with embodiments of the present invention.

FIG. 6 depicts changes in biochemical bone turnover markers in response to treatment, in accordance with embodiments of the present invention. FIG. 6 shows changes in serum osteocalcin (s-OC) (A), serum procollagen type 1 N-telopeptide (s-P1NP) (B), urinary deoxypyridinoline (u-DPD) (C), and cross-linked carboxyterminal telopeptides (s-CTx) (D) overtime in response to treatment for 12 weeks. Values are mean±SD (n=16 in each group). SHAM=sham-operated; OVX=ovariectomized; ALN=alendronate; OVX 15=OVX treated with lycopene (15 mg/kg body weight/day); OVX 30=OVX treated with lycopene (30 mg/kg body weight/day); OVX 45=OVX treated with lycopene (45 mg/kg body weight/day); and ALN=OVX treated with alendronate (2.0 ug/kg body weight per day), respectively.

Figure 7:
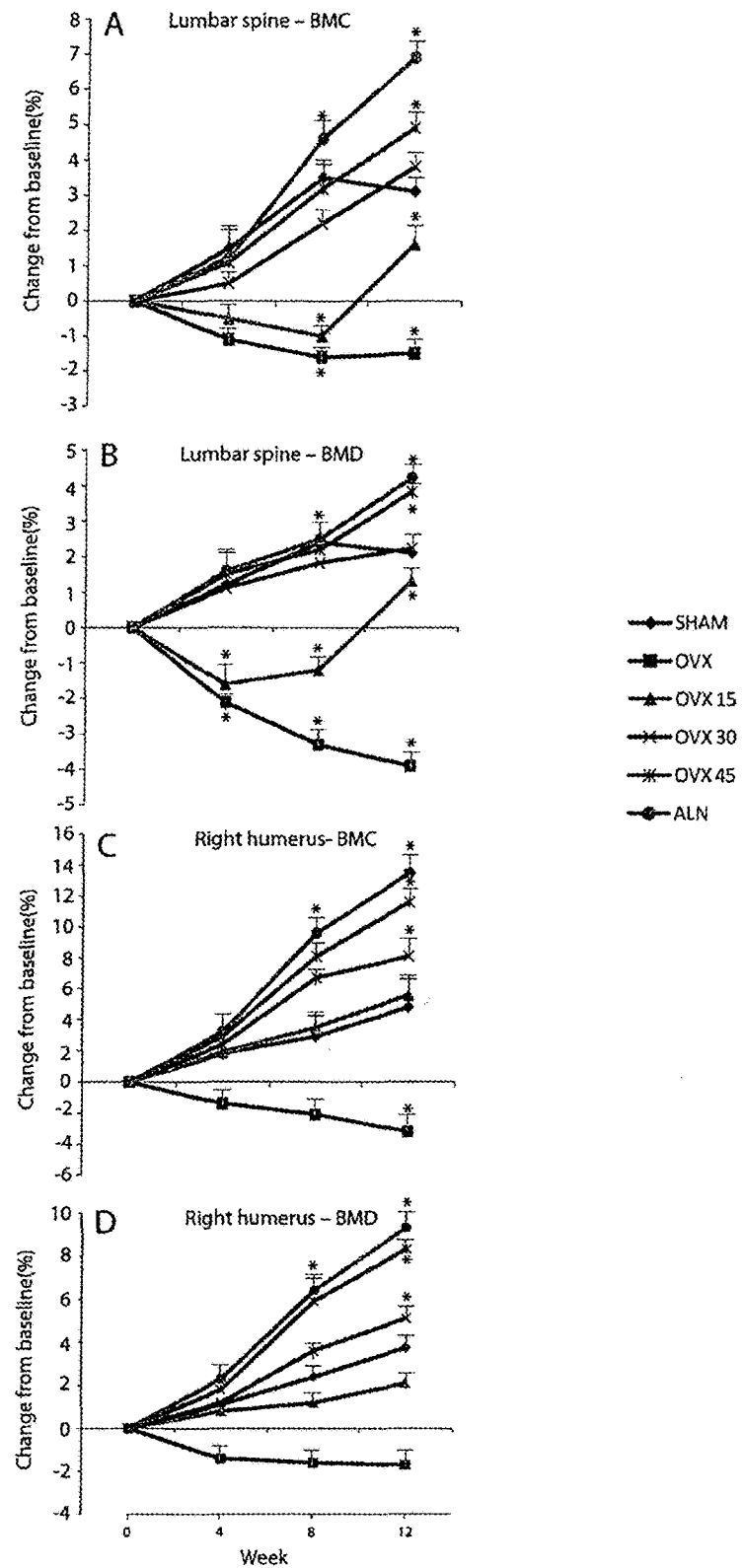
FIG. 7 depicts changes in bone mineral content (BMC) and bone mineral density (BMD) in response to treatment, in accordance with embodiments of the present invention.

FIG. 7 depicts changes in bone mineral content (BMC) and bone mineral density (BMD) in response to treatment, in accordance with embodiments of the present invention. FIG. 7 shows changes overtime (as percent change from baseline values) in bone mineral content (BMC; A, C) and density (BMD; B, D) for lumbar spine and hummers as determined by DXA during treatment for 12 weeks. Values are meant ±SD for 16 rats in each group. DXA=dual-energy X-ray absorptiometry. SHAM=sham-operated; OVX=ovariectomized; ALN=alendronate; OVX 15=OVX treated with lycopene (15 mg/kg body weight/day); OVX 30=OVX treated with lycopene (30 mg/kg body weight/day); OVX 45=OVX treated with lycopene (45 mg/kg body weight/day); and ALN=OVX treated with alendronate (2.0 ug/kg body weight per day), respectively.

Figure 8:
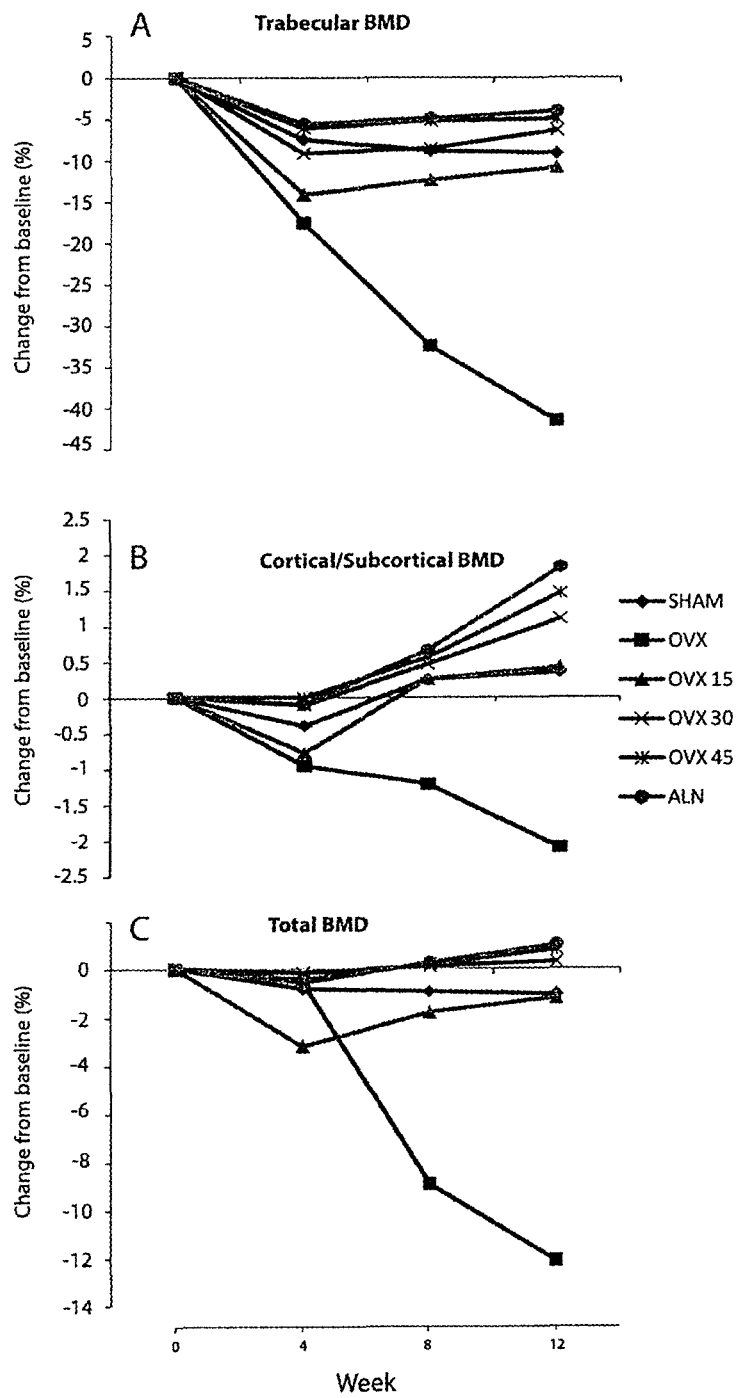
FIG. 8 depicts changes in trabecular, cortical/subcortical and total BMD in response to treatment, in accordance with embodiments of the present invention.

FIG. 8 depicts changes in trabecular, cortical/subcortical and total BMD in response to treatment, in accordance with embodiments of the present invention. FIG. 8 shows changes overtime (as percent change from baseline values) in trabecular (A), cortical/subcortical (B), and total (C) bone mineral density (BMD) at tibia metaphysic as determined by pQCT during treatment for 12 weeks. Values are mean±SD for rats in each group. SHAM=sham-operated; OVX=ovariectomized; ALN=alendronate; OVX 15=OVX treated with lycopene (15 mg/kg body weight/day); OVX 30=OVX treated with lycopene (30 mg/kg body weight/day); OVX 45=OVX treated with lycopene (45 mg/kg body weight/day); and ALN=OVX treated with alendronate (2.0 ug/kg body weight per day), respectively.

Figure 9:
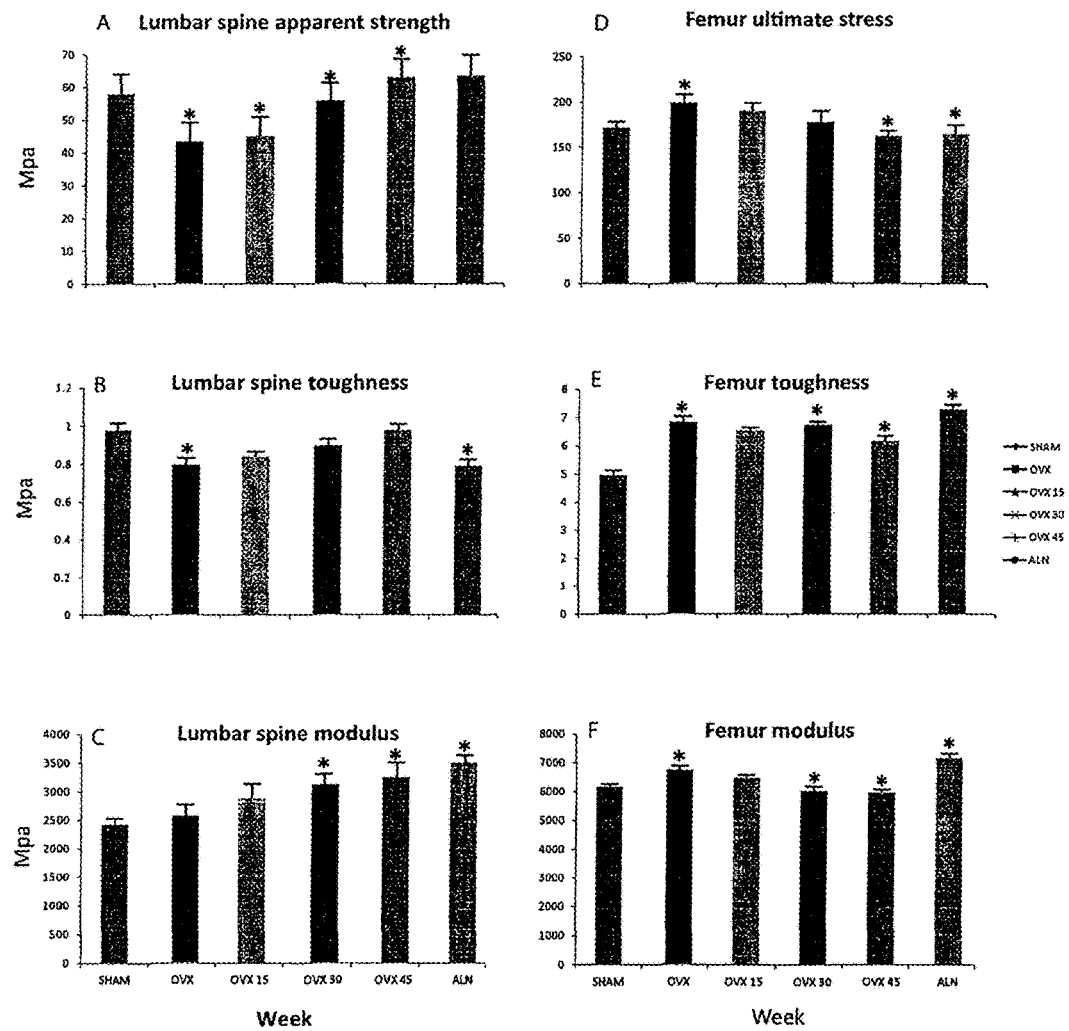
FIG. 9 depicts biomechanical parameters for lumbar spine and femur in response to treatment, in accordance with embodiments of the present invention.

FIG. 9 depicts biomechanical parameters for lumbar spine and femur in response to treatment, in accordance with embodiments of the present invention. FIG. 9 shows bone biomechanical values for the lumbar spine [apparent strength (A), toughness (B), modulus (C)] as determined by compression testing and for the femur [ultimate stress (D), toughness (E), modulus (F)] as determined by three-point bending. Values are mean±SD. SHAM=sham-operated; OVX=ovariectomized; ALN=alendronate; OVX 15=OVX treated with lycopene (15 mg/kg body weight/day); OVX 30=OVX treated with lycopene (30 mg/kg body weight/day); OVX 45=OVX treated with lycopene (45 mg/kg body weight/day); and ALN=OVX treated with alendronate (2.0 ug/kg body weight per day), respectively.

Figure 10:
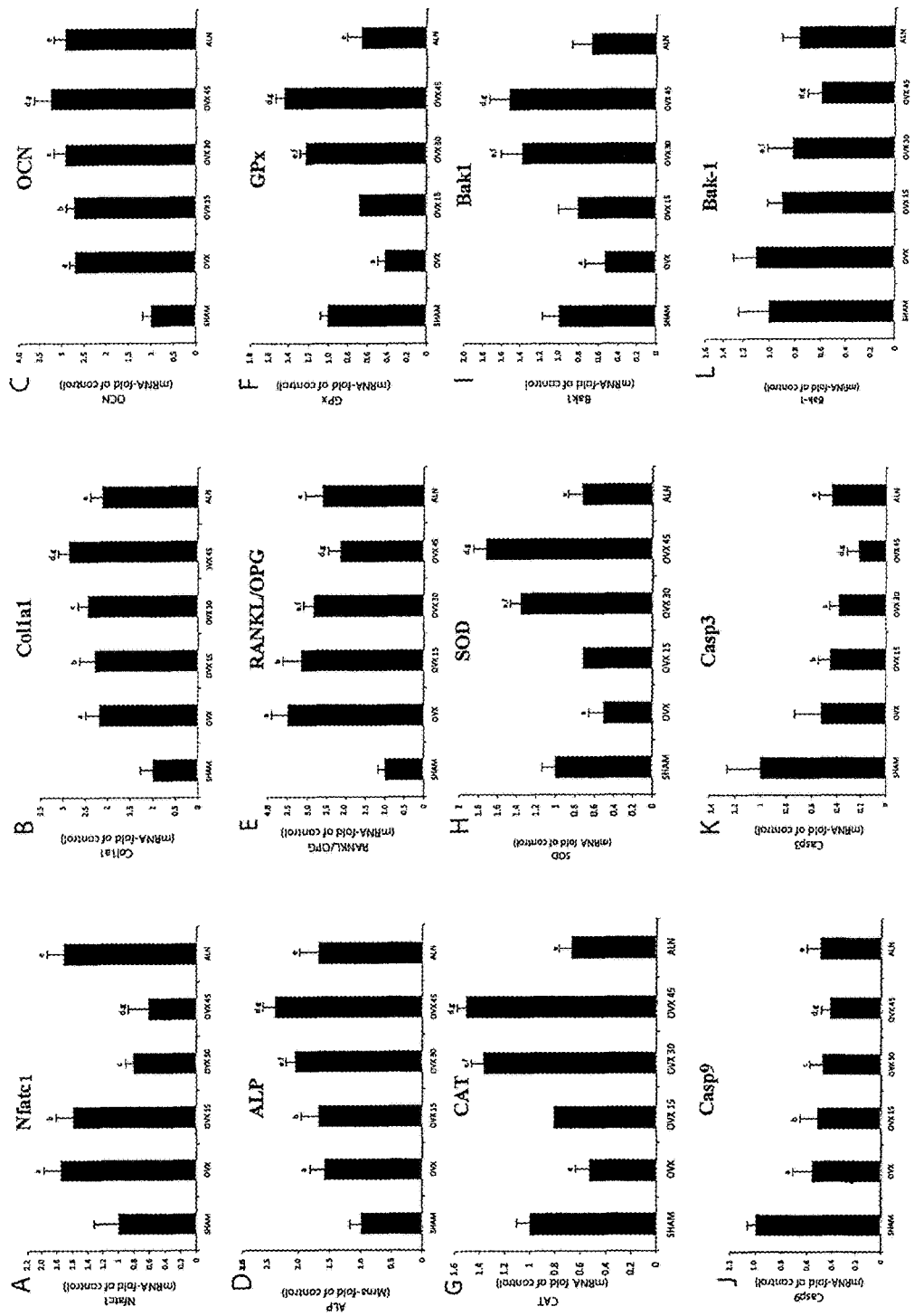
FIG. 10 depicts qCT-PCR analysis of genes involved in osteoblast activity, osteoclastogenesis, apoptosis and oxidative stress enzymes, in accordance with embodiments of the present invention.

FIG. 10 depicts qCT-PCR analysis of genes involved in osteoblast activity, osteoclastogenesis, apoptosis and oxidative stress enzymes, in accordance with embodiments of the present invention. Bone marrow (A) was analyzed for relative mRNA abundance of the osteoclastogenesis gene factor of activated T-cells (Nfatc1), while the flushed femur (B-D) was used to examine genes involved in osteoblast activity and function: type 1 collagen (Col1a1), osteocalcin (Ocn), alkaline phosphatase (Alp), osteoprotegerin (Opg), and receptor activator for NF-kappa B ligand (Rankl) in sham-operated (SHAM) and ovariectomized (Ovx) rats treated with placebo or lycopene (15, 30 and 45 mg/kg body weight per day) or alendronate (ALN) (2.0 ug/kg body weight per day) for 12 weeks. Bone marrow (F-H) was analyzed for relative mRNA abundance of oxidative enzyme: glutathione peroxidase (GPx), superoxide dismutase (SOD) and catalase (CAT) in sham-operated (SHAM) and ovariectomized (Ovx) rats treated with placebo or lycopene (15, 30 and 45 mg/kg body weight per day) or alendronate (ALN) (2.0 ug/kg body weight per day) for 12 weeks. Bone marrow (I) and the flushed femur (J-L) were analyzed for relative mRNA abundance of apoptotic genes. Genes of interest including, B-cell lymphoma homologous antagonist/killer (Bak1), caspase-3 (Casp3) and -9 (Casp 9) in sham-operated (SHAM) and ovariectomized (Ovx) rats treated with placebo or lycopene (15, 30 and 45 mg/kg body weight per day) or alendronate (ALN) (2.0 ug/kg body weight per day) for 12 weeks. Bars represent the mean±SD for 10 rats in each group.

Example 1: Preparation of Lycopene/OEGCG Nanoparticles

In a typical experiment, OEGCG (20 mg) and lycopene (10 mg) were first dissolved in 5 mL of acetone/ethanol yielding a 4 mg/mL OEGCG solution. Note that slight increase in the temperature of the polymer solution to 50° C. to dissolve lycopene was achieved. Subsequently, the lycopene solution was added drop wise into 30 mL of water containing polyethylene glycol sorbitan monooleate (20 mg) and sonicated for 10 min. The entire solution was then sonicated for ~30 s using a probe sonicator. The residual acetone and ethanol was removed under vacuum rotary evaporation at 40° C. The NP suspension was washed once with water using ultrafiltration centrifugation (9800×g, at 4° C. for 60 min) and resuspended.

Example 2: Preparation of Lycopene/PLGA Nanoparticles Via Nano-Precipitation

PLGA (20 mg) and lycopene (4 mg) were first dissolved in 5 mL of acetone yielding a 4 mg/mL polymer solution. Note that the temperature of the polymer solution was slightly increased to 50° C. to dissolve lycopene. Subsequently, the remaining steps were followed as described above.

Example 3: Lycopene Nanocrystals (<1 micrometer size) dispensed in olive oil and dispensed in Soft gels.

Example 4: Solid Lipid Nanoparticles (SLN)

5 mg lycopene added in small vial and oil added with or without DHA and/or EPA. Olive oil/Cremopher EL, Cremopher RH 40, Tween 20/Glycerol. DHA and/or EPA+Lycopene in olive oil, water/Cremopher EL or Cremopher RH 40/Glycerol plus Lycopene or combination thereof.

Example 5: Preparation of Chitosan-Coated Lycopene/OEGCG Nanoparticles

One mg of chitosan oligosaccharide lactate was dissolved in 1 mL water. Then this chitosan solution was added into the lycopene/OEGCG NPs solution under sonication and incubated for 30 min at room temperature. The solution was then washed once with water using centrifugation (14800×g at 4° C. for 60 min) and resuspended (FIG. 1).

Example 6: Nanoparticles Characterization

Proton nuclear magnetic resonance ($^1$H NMR) spectra were recorded on a Bruker Avance 800 MHz spectrometer at Rensselaer Polytechnic Institute (FIG. 2). The spectra were recorded in DMSO-d6 with water as the internal standard in $^1$H NMR spectra. Transmission electron microscopy (TEM) studies were carried out using a JEOL 2010 transmission electron microscope with an accelerating voltage of 80 kV (FIG. 3). TEM samples were prepared by casting the suspension of assemblies on a carbon-coated copper grid (300 mesh). Fourier transform infrared spectroscopy (FT-IR) investigations were carried out using a Thermo Nicolet Avatar 330 FT-IR spectrometer (FIG. 4). The hydrodynamic diameters of lycopene NPs and c-potential were measured with dynamic light scattering (DLS) using a Zetasizer Nano ZS dedicated c-potential analyzer (Malvern Instruments, Worcestershire, UK), and each batch was analyzed in triplicate.

Example 7: Freeze Drying

Freeze drying was employed as a means to impart stability or improve shelf life of the developed formulations. In brief, 2 mL of the NP suspension was placed in 20 mL glass vials. Sucrose 10% (w/v) was added as a cryo-protectant to preserve the NP properties during the freezing step. Then the solution was frozen at −80° C. for 12 hours, and afterward it was sublimated for 24 hours under pressure of 0.110 mPa at room temperature. Finally, the NPs were collected and preserved in a Freezer for later evaluation and analysis.

Example 8: Determination of the Lycopene Encapsulation Efficiency and Loading Rates The encapsulation efficiency of lycopene NPs was determined by analyzing the lycopene loading in the NPs compared to the lycopene fed initially.[26] After lyophilization, the weighed NP powder was dispersed in 15 mL of hexane-water (9:1, v/v), followed by sonication for 10 min until no color was observed in the water phase. Subsequently, the resulting solution was centrifuged at 9,600×g for 10 min. The amount of lycopene in the hexane was determined at 475 nm using a NanoDrop 2000 UV-Vis spectrophotometer (Thermo Scientific, Waltham, Mass.) and a calibration curve (Figure S1). Lycopene encapsulation efficiency and lycopene loading were calculated from Eqs. 1 and 2, respectively:

$$\text{Entrapment efficiency (\%)} = \frac{\text{weight of lycopene in nanoparticles}}{\text{weight of lycopene fed initially}} \times 100 \quad (1)$$

$$\text{Lycopene loading (\%)} = \frac{\text{weight of lycopene in nanoparticles}}{\text{weight of nanoparticles}} \times 100 \quad (2)$$

TABLE 1

Characterizations of the effects of lycopene loading on OEGCG/chitosan nanoparticles (NPs)

| Lycopene loading[a] | Particle size (nm) | PDI[b] | ζ potential (mv ± SD)[c] | EE %[d] | Loading of NPs % |
|---|---|---|---|---|---|
| 0 | 135 | 0.25 | 50.4 ± 3.8 | — | — |
| 11 | 152 | 0.21 | 58.3 ± 4.2 | 89 | 9 |
| 15 | 225 | 0.20 | 50.9 ± 3.5 | 85 | 12 |
| 20 | 276 | 0.26 | 44.2 ± 4.7 | 81 | 15 |

[a]Lycopene loading to polymer weight (w/w %);
[b]polydispersivity/polydispersibility index;
[c]ζ-potentials were determined in deionized water;
[d]EE, the entrapment efficiency was determined at 475 nm

Example 9: In Vivo Animal Study

Male C57BL/6 mice, 6-8 weeks old housed 5-6 per cage in a room maintained at 20±2° C. with a humidity of 50±10% and a 12 hour light-dark cycle. The animals were fed a standard pelleted mouse chow. Lycopene in different nanoformulations versus lycopene dispensed in oil were administered by oral gavage and blood samples (30 µl) were taken at 0.5, 1, 3, 6, 12, and 24 hours (using a heparinized capillary) post-administration for PK profiles using established LC-MS/MS. LC-MS/MS analysis was performed on mouse plasma samples with an API 4000 triple quad mass spectrometer (ABSCIEX, Framingham, Mass.) configured with a Shimadzu LC-20AD pumping system, a SIL-20AC autosampler, and a CTO-20AC column oven. The system was operated under Analyst 1.63 control (ABSCIEX). The chromatographic separation of lycopene was achieved on a Phenomenex Kinetx EVO C18-100 Å, column, 50×2.1 mm ID, packed with 2.6 µm particles. The samples were eluted with isocratic acetonitrile/methyl-tert-butyl ether (MTBE) (95:5 v/v) at a flow of rate of 0.5 mL/min.[28] The total run time was 4 min. The column oven temperature was kept at 40° C. and sample injection volume was 10 µl. The MRM transition for lycopene was m/z 537.4>282.4 and for internal standard reserpine it was m/z 609.4>195.1. The instrument was operated in a positive ion atmospheric pressure chemical ionization (APCI) mode with a turbo ion spray source. The parameters for the operation were: curtain gas, 20 psi; heated nebulizer temperature 350° C.; needle current, 3.0 µA; gas 1, 65 psi; de-clustering potential, 71 V (lycopene), 71 V (reserpine); EP, 10 V; CE, 11 V (lycopene), 51 V (reserpine); CXP, 20 (lycopene), 14 V (reserpine); and CAD gas, 6.0 V. The dwell time for each transition was 150 ms. A calibration curve for the lycopene was prepared by spiking lycopene at seven different concentrations from 10 ng/mL to 500 ng/mL into 20 µL plasma. Lycopene was extracted followed by LC-MS/MS analysis. Ratios of peak areas to the corresponding internal standard were plotted against lycopene concentrations. The calibration curve fitting was linear regression, and the standard value was outside ±20% of the theoretical value. In order to pass acceptance criteria, no more than two standard levels or two adjacent standard levels in the calibration curve could fail. Pharmacokinetic data analysis was carried out using WinNonlin software (version 5.2, Pharsight, Mountain View, Calif.) with a non-compartmental model and one compartment first order, on lag time and first order elimination. The area from 0 to 24 hours under the lycopene concentration time curve was used to determine the AUC. All the other parameters including $C_{max}$, $T_{max}$ and $t_{1/2}$ were determined with WinNonlin software as well (Table 2 and FIG. 5).

TABLE 2

Characterizations of pharmacokinetic parameters of lycopene after oral administration of pure lycopene dissolved in olive oil, lycopene/OEGCG NPs, lycopene/OEGCG/chitosan NPs, lycopene/PLGA NPs and lycopene/PLGA/chitosan NPs.

| Formulation | AUC (ng h/mL)[a] | $C_{max}$ (ng/mL)[b] | $T_{max}$ (h)[c] | MRT (h)[d] | $t_{1/2}$ (h)[e] |
|---|---|---|---|---|---|
| Lycopene/olive oil | 268.1 | 22.4 | 0.5 | 10.5 | 15.6 |
| Lycopene/OEGCG NPs | 354 | 22.8 | 1.0 | 11.1 | 32.0 |
| Lycopene/OEGCG/Chitosan NPs | 5114.9 | 382.3 | 0.5 | 11.5 | 23.1 |
| Lycopene/PLGA NPs | 141.2 | 39.0 | 0.5 | 5.55 | 6.57 |
| Lycopene/PLGA/Chitosan NPs | 181.0 | 40.7 | 0.5 | 7.86 | 17.7 |

[a]area under the concentration time curve;
[b]maximum plasma concentration;
[c]time taken to reach $C_{max}$;
[d]mean residence time;
[e]time required for the concentration of the drug to reach half of its original value.

Example 10: Animals and Experimental Design

A total of 264 Wistar female rats, ~6 months old, were supplied by the Animal House at King Fahd Medical Research Center (KFMRC), KAU. Rats were housed in individual cages and maintained at 22° C. with a 12-h light/dark cycle. During the study period, rats were given standard rodent chow diet ad libitum (commercial rat cubes containing approximately 18% protein, 3% fat, 77% carbohydrate, and 2% of an inorganic-salt mixture with a vitamin supplement by weight, supplied by Grain Silos and Flour Mills Organization, Jeddah, Saudi Arabia) and water until the onset of intervention. Prior to surgery, rats were anesthetized with ketamine [(10% ketamine hydrochloride (80 mg/kg body weight), Cayman Chemical, Michigan, USA] and xylazine [(2% xylazine hydrochloride, 10 mg/kg body weight), Sigma-Aldrich Co., St. Louis, USA]. A single longitudinal skin incision was made on the dorsal midline at the level of the kidneys and both ovaries were ligated and removed to produce an ovariectomy in all OVX group animals. A SHAM-operated group, acting as a negative control for the effect of ovariectomy on bone parameters, underwent bilateral laparotomy, during which the ovaries were exposed but remained intact. Vaginal smears were collected 3-10 days after surgery to confirm the effects of the surgery: all groups (except the SHAM group) demonstrated successful ovariectomy. The lycopene-supplemented groups were given lycopene (15, 30 and 45 mg/kg body weight per day) dissolved in corn oil by daily intra-gastric administration for the experimental period of 12 weeks. The SHAM, OVX and ALN control groups were given the same volume of corn oil without lycopene treatment. Rational for lycopene dose selection is based on previous studies, which have showed lycopene supplementation at these doses, its bioavailability, as well as its protective effect against oxidative stress. A 12-week randomized placebo-controlled study in order to examine the protective effects of lycopene supplementation on bone mass and fragility in OVX rats was concluded. Prior to surgery, body weight and bone mineral density (BMD) were obtained for all animals. Rats were randomized using a computer-generated randomization code into one of six groups: (1) sham-operated (SHAM; n=44); (2) ovariectomized control (OVX; n=44); (3) OVX lycopene-supplemented (15 mg/kg body weight per day) (n=44); (4) OVX lycopene-supplemented (30 mg/kg body weight per day) (n=44); (5) OVX lycopene-supplemented (45 mg/kg body weight per day) (n=44) and (6) OVX alendronate-treated (ALN) [2.0 µg/kg body weight per day subcutaneously (sc)] (n=44). Alendronate is an anti-resorptive agent for the treatment of osteoporosis and was used as a positive therapy control. This dosage was based on preclinical studies that demonstrated significant increases in bone mass and strength [28], and is comparable to the 20 mg/kg/day dosage prescribed to treat osteoporosis. All OVX groups were pair-fed with the SHAM group throughout the study to avoid the possible effects of ovariectomy-induced over-consumption and subsequent excessive weight gain. Treatment started 1 week after the surgery: this period of rest allowed the rats to recover from the stress associated with the surgery. In addition, after surgery, rats were administered Diclofenac sodium injection (20 mg/Kg body weight) to reduce the pain associated with the surgery. Rats were weighed and examined daily. Blood and urine samples were collected at baseline, during, and at the end of treatment for measurement of various BTMs and other analytes. In vivo dual energy x-ray absorptiometry (DXA) measurements were made for the bone mineral content (BMC) and BMD of the whole body, lumbar spine ($L_1$-$L_4$), and the right humerus, together with body composition at 12 weeks of treatment. One day following the post-test DXA assessments (at 12 weeks, 16 rats in each group), animals were euthanized by decapitation and right and left femurs were extracted for further biomechanical and histomorphometric analyses. Blood and urine samples were collected from all experimental groups to measure biochemical analytes and BTMs at baseline and 4, 8, and 12 weeks of treatment. Peripheral Quantitative CT (pQCT) scans were made of the proximal tibia metaphysis and the diaphysis. In vivo micro-computed tomographic (µCT) scans of the proximal tibia were obtained during the treatment period to monitor changes in bone mass and microarchitecture. Ex vivo µCT measurements were obtained for the third lumbar spine vertebra ($L_3$) and right femur for bone mass and architectural evaluations, as well as cortical mineral density. Histomorphometric measurements of surface-based bone turnover were obtained from the proximal tibia metaphysis and the mid-shaft of the tibia from all rats by labeling the skeleton with calcein 7 and 2 days prior to euthanasia. Bone mechanical properties were examined by compression tests of the $L_3$ and bending tests of the right femur. Details of each measurement are presented below. All procedures were approved by CEOR Ethical Committee in agreement with local Institutional Animal Care and Use and are in conformity with the international guidelines on the ethical use of animals.

Example 11: Blood and Urine Sampling

During the experimental period at baseline, 4 weeks, and 8 weeks, blood and 24 hour urine samples were collected. All rats were fasted overnight prior to sampling. The following day, after anesthesia with diethyl ether, blood samples were collected from the tail artery of the rat. Blood samples were centrifuged at 2,500 g for 15 min at 4° C. to extract serum. Serum and urine samples were stored in liquid $N_2$ until analysis of BTMs and other analytes. At the end of the experimental period (12 weeks), all rats were fasted overnight and 24 h urine samples were collected. The following day, after anesthesia with diethyl ether, blood samples were taken from the abdominal aorta and serum was separated as described previously. Livers were extirpated immediately following blood collection and weighed, frozen, and stored in liquid $N_2$. The lumbar spine, tibia, and femurs of each rat were isolated by dissection, freed from adjacent soft tissue, and processed for further studies as described below.

Example 12: Measurements of Biochemical BTMs

The following BTMs were measured in rat sera using commercially available kits designed to measure rat BTMs: serum osteocalcin Rat-MID Osteocalcin (s-OC) (Immunodiagnostic Systems, Boldon, UK); serum N-terminal propeptide of type 1 collagen (s-PINP) EIA (Immunodiagnostic Systems, Boldon, UK); serum crosslinked carboxyterminal telopeptides (s-CTX-1) RatLaps (Immunodiagnostic Systems, Boldon, UK), and urinary deoxypyridinoline (u-DPD) (Osteolinks-DPD, DS Pharma Biomedical Co., Japan). Urine samples for DPD were collected from animals fasted overnight in metabolic cages and corrected for creatinine concentration. Measurements were made using an automated immunoassay system. The intra-assay and inter-assay coefficients of variations (CVs) ranges were 4.2-5.3% and 5.5-6.4%, respectively.

Example 13: Measurements of Serum and Liver Lycopene

Levels of serum and liver lycopene were measured using high-performance liquid chromatography (HPLC), as described previously [30,31], using a Waters 2695 Alliance HPLC System and a Waters 2998 PDA detector (Milford, Mass., USA). Approximately 0.25 mg liver was homogenized in 2 ml absolute ethanol containing 1 g/L butylated hydroxytoluene with an ultrasonic processor (model UP-400S, Hielscher Inc., NJ, USA). The homogenate was treated with 0.5 ml of KOH for 30 min at 70° C. for saponification. The sample was then cooled to room temperature, washed with 1 ml of distilled $H_2O$, and then extracted with 3 ml of n-hexane three times. The hexane extract volume was brought up to 10 ml with n-hexane. One milliliter of the extract was evaporated to dryness under $N_2$ at 40° C. and dissolved in 50 µl of tetrahydrofuran with the addition of 150 µl of methanol. Finally, 100 µl of the prepared solution was injected into the HPLC system for analysis of lycopene. Serum samples (2 ml mixed with distilled $H_2O$) were extracted with n-hexane. The hexane extract was evaporated to dryness, dissolved, and injected into the HPLC system as described for liver tissue samples. Separation was performed using a RP-18 GP Column (Ø4.0×250 mm) with methanol/tetrahydrofuran (75:25, v/v) as the mobile phase at a flow rate of 1.0 ml/min. An external standard of lycopene (Sigma-Aldrich Co. St. Louis, USA) was used a reference.

Example 14: Measurements of Other Biochemical Analytes

Serum estradiol ($E_2$), follicular stimulating hormone (FSH), luteinizing hormone (LH), parathyroid hormone (PTH), creatinine, calcium, phosphate, alanine aminotransferase (ALT), and aspartate aminotransferase (AST) were measured by kits and reagents supplied by Ortho-Clinical Diagnostics, USA using a Vitros 250 Chemistry System Autoanalyzer (Ortho-Clinical Diagnostics, Johnson & Johnson Co., USA).

Example 15: Measurements of Plasma Glutathione Peroxidase and Urinary 8-hydroxy-2-deoxyguanasine (8-OHdG) Levels Due to the potential effect of lycopene treatment on oxidative stress status, along with the possible impact this may have on osteoblast and osteoclast activity, plasma glutathione peroxidase (GPx), superoxide dismutase (SOD) and catalase (CAT) activities were determined using a commercially available kits (Cayman Chemical, Ann Arbor, Mich., USA). All samples were diluted 1:2 and the assay was performed according to the manufacturer's instructions. The intra- and inter-assay CVs for the GPx, SOD and CAT assays ranged from 4.8% to 7.3%, respectively. Levels of urinary 8-OHdG, which is an established marker of oxidative DNA damage in vivo, were determined. The 8-OHdG was extracted from 1 ml of urine with an Oasis® HLB 3 cc (60 mg) cartridge. The eluent was dried under an ultra-pure N2 stream and reconstituted in buffer (10 mM ammonium acetate in 2% methanol, pH 4.3) for analysis with the HPLC system. Authentic standard 8-OHdG retention times and response patterns were used for qualification and determination of calibration curves. The limit of detection for 8-OHdG was 1 ng/ml. The amount of 8-OHdG excreted in urine was adjusted by urinary creatinine measurement, and the intra- and inter-assay CVs for the urinary 8-OHdG assays were 6.2% and 7.4%, respectively Example 16: RNA Extraction and Quantitative Real-Time PCR After the rats were euthanized, femurs were excised from each animal and cleaned of soft tissue including cartilage, tendons, and ligaments. Alterations in the expression of genes associated with bone metabolism, apoptosis, and oxidative stress were examined in bone by quantitative real-time PCR (qRT-PCR). Total RNA was extracted from pulverized-flushed femurs (Spex 6770 Freezer Mill, Metuchen, N.J., USA) and bone marrow using Trizol Reagent according to the manufacturer's instructions (Life Technology, Rockville, Md., USA). The hard tissue, an osteoblast rich site, and bone marrow, a site in which osteoclasts reside, were examined. RNA from the bone marrow was further purified with a second Trizol extraction. The $A_{260}/A_{280}$ ratio was determined using a Nanodrop Spectrophotometer (Nanodrop, Rockland, Del., USA) to determine the quantity of RNA, and gel electrophoresis was performed to verify the quality of all RNA samples extracted. qRT-PCR was performed using 2 µg of total RNA pre-treated with DNase I and subjected to reverse-transcription (Superscript II, Invitrogen, Carlsbad, Calif., USA). cDNA (50 ng) was used for each qRT-PCR reaction and all reactions were assayed in duplicate using SYBR green chemistry (SABiosciences, Valencia, Calif., USA) on the Applied Biosystems 7900HT Fast Real-Time PCR System (Foster City, Calif., USA). All qRT-PCR results were assessed by the comparative cycle number at threshold ($C_T$) method using cyclophilin b (Cyclo) as the invariant control. Primer sequences were designed on Genebank database or published species-specific sequences. (Supplementary Table 1). Gene expression of nuclear factor for activated T cells (Nfact1), alkaline phosphatase (Alp), B-cell lymphoma homologous antagonist/killer (Bak1), caspase-3 (Casp3), caspase-9 (Casp9), catalase (CAT), type I collagen (Colla1), glutathione peroxidase (GPx), osteocalcin (Ocn), osteoprotegerin (Opg), and receptor activator for NF-kappa B ligand (Rankl), and superoxide dismutase (SOD1) were analyzed.

Example 17: Bone Mass Measurements by DXA and pQCT

The BMD, BMC, and areas of the lumbar spine ($L_1$-$L_4$), right humerus and whole body were measured by in vivo DXA scans (Hologic QDR Discovery A, Denver, Colo., USA). The proximal tibia metaphysis and diaphysis were scanned using pQCT scans [XCT Research SA, SA+bone scanner (Stratec Medizintechnik GmbH, Pforzheim, Germany) using the software version 5.50D]. The scans at the metaphysis (a site rich in trabecular bone) were examined for total slice, trabecular, and cortical/subcortical bone area, BMC, and BMD (ContMode 2, PeelMode 20, 40% trabecular area). The scans at the diaphysis (a site rich in cortical bone) were examined for total slice and cortical bone area, cortical BMC, BMD, periosteal circumference, endosteal circumference, and cortical thickness (CortMode 2, threshold 0.930 l/cm). All DXA and pQCT analyses were performed at baseline, 4, 8, and 12 weeks of treatment using 16 rats in each group.

Example 18: Ex Vivo Bone Mineral Density and Geometry

At the end of the 12-week experimental period, isolated $L_3$ vertebrae and the whole right femur were covered with normal saline and frozen at −20° C. Bone specimens were thawed overnight at −4° C. and used to normalize bone strength data to bone size using pQCT scanning. For $L_3$ compression analysis, the pQCT scans were performed at the mid-section of the vertebral body of the lumbar spine using ContMode 2 and PeelMode 20 (trabecular area 50%). For the femur, the pQCT scans were performed at the expected breaking point in 3-point bending using CortMode 2 (threshold 0.930 l/cm) analysis. Bones from a total of 16 rats were used in each group.

Example 19: Biomechanical Testing

At the end of the 12-week experimental period, biomechanical testing of bone specimens was performed using the 858 Mini Bionex Servohydraulic Test System (Model 242-MTS System Corporation, Eden, Prairie, Minn., USA) and data were analyzed using Test Works V 3.8 A for TestStar v4.0C (MTS System Corporation). For the $L_3$ vertebral body assessment, specimens were tested in compression to failure. A loading rate of 20 mm/min was used to obtain both load and displacement data. Apparent strength and modulus values were computed using the peak load, stiffness, individual vertebral body height, and the cross-sectional area obtained from pQCT scans. Accordingly, the work-to-failure was calculated from the area under the curve (AUC) and the toughness values were computed using the cross-sectional area obtained by pQCT scans and vertebral body height. For the whole right femur, biomechanical testing was performed at three-point bending failure to assess bone strength. The actuator was set at a rate of 1 mm/s until failure was observed, and data for load and displacement were obtained. To determine peak load, a load versus displacement curve was converted to ultimate stress using the radius, cross-sectional moment of inertia, and the span. The work-to-failure was calculated from the AUC, and toughness was then computed. Both stiffness (defined as the slope of the linear/elastic region of the load versus displacement curve) and modulus were determined using the moment of inertia collected from the pQCT data and span.

Example 20: µCT Analysis

To assess trabecular (using the left proximal tibia) and cortical (using the right mid-femur) bone parameters, 3-dimensional µCT analysis was performed using a Micro-CT 40 scanner (software version 6.0; Scanco Medical AG, Bruttiselen, Switzerland). A total of 16 rats from each group were used. All analysis and terminology conform to American Society of Bone and Mineral Research (ASBMR) guidelines.

Example 21: Histomorphometry

All histomorphometric data were collected from 12 rats from each group, using a Bioquant image analyzer (Bioquant Osteo II; Bioquant Image Analysis Corporation, Nashville, Tenn., USA). At 7 days and 2 days prior to necropsy, rats were injected with 8 mg/kg (sc) of calcein green (Sigma-Aldrich Co., St Louis, USA). Bone specimens were preserved in 10% neutral buffered formalin and then stored in 700 alcohol. Bones were then processed undecalcified through steps of dehydration using alcohol and xylene, and embedded into methylmethacrylate. To study trabecular bone, sections from two levels were cut from the right proximal tibia (i.e., frontal plane). Sections were stained by Goldnor's trichome or left unstained. To examine cortical bone, two levels of transversally cut ground and unstained sections of the diaphysis were obtained from the tibiofibular junction of the right tibia. All analyses and terminology conform to recommendations by the ASBMR; however, no correction factor was considered for section obliquity during the calculation of trabecular thickness, and mineral apposition rate (MAR). Variables related to the trabecular bone microarchitecture were determined according to the parallel plate model. Parameters for mineralizing surface (MS/BS), endocortical labeled surface (Ec.L.Pm/Ec.Pm; Pm=perimeter), and periosteal labeled surface (Ps.L.Pm/Ps.Pm) were calculated as half-single plus double-label surfaces. When it was not possible to determine the MAR, the variable was reported as 0.6 μm/d; this value represents the smallest measurable inter-label width according to the exclusion criteria and reflects the assumption of minimal bone turnover.

Example 22: Statistical Analysis

Results are presented as means (+SD) and data were analyzed using SPSS Statistical Package (version 17.0 for Windows Smart Viewer) (SPSS Inc., 2000 Mapinfo Corp., Tokyo, N.Y., USA). For in vivo densitometry data (DXA and pQCT), results are presented as percentage change from baseline. Group differences were examined by ANOVA during the supplementation period. When the overall ANOVA F-test was significant (≤0.05), then the Dunnett's t-test was applied for comparison analysis among the groups.

Body Weight, Uterine Weight, Body Composition, and Serum Lycopene Levels:

Moderate body weight gain was evident in all OVX groups with no significant differences observed in final body weights among the OVX groups. Lycopene treatment did not significantly influence the final body weight, body weight gain, or food intake (data not shown). Body composition analysis by DXA, however, showed that while fat mass increased about 22% in the OVX control group, groups with higher dosages of lycopene had 8.9% and 16.4% decreases in fat mass (P<0.003), lean body mass did not change significantly. No degeneration or hypertrophy of internal organs, including muscle and bone, was evident in lycopene-treated rats. The success of the surgical intervention was confirmed by increased uterine atrophy among the OVX groups, as compared to the SHAM control group.

Lycopene treatment (30 and 45 mg/kg body weight per day) significantly increased uterine weight as compared to OVX alone. There was no detectable lycopene in serum or livers from the SHAM or OVX control rats. Lycopene was detected in serum and livers of rats treated with lycopene in a dose-dependent fashion. Serum lycopene (nmol/L) levels were 71.45±4.65 at 12 weeks with treatment of 45 mg/kg body weight per day. Liver lycopene levels in the 30 and 45 mg/kg body weight per day groups were significantly higher than that of the 15 mg/kg body weight per day group. Daily lycopene intake was significantly correlated with serum lycopene levels (r=0.426, P<0.001) and liver lycopene concentration (r=0.452, P<0.001) in the lycopene-treated groups.

Serum Minerals, Enzymes, and Hormones:

No significant differences in serum calcium, phosphate, albumin, AST, ALT, or creatinine between the SHAM group and other groups were observed. Compared with SHAM control, serum estradiol ($E_2$) levels were markedly decreased (P<0.001) in the OVX group. Notably, serum $E_2$ significantly increased in a dose-dependent manner in the OVX lycopene-treated groups (P<0.001). Serum PTH levels were similar in both the SHAM and most OVX groups; however, the 45 mg/kg body weight per day lycopene and the ALN groups exhibited significantly higher serum PTH values than that observed in other groups (P<0.001).

Plasma GPx, SOD and CAT Activities and Urinary 8-OHdG Levels:

Evaluation of systemic antioxidant activity revealed that the OVX control group had significantly lower (P<0.05) plasma GPx activity as compared with the SHAM group but lycopene treatment significantly increased GPx activity (30.6-57.2%) compared to the OVX control (P<0.001 in each case). The ALN group showed similar GPx activity to the OVX control group. Similar results were obtained for plasma SOD and CAT activities to that observed for plasma GPX (data not shown). The effect of lycopene treatment on DNA oxidative stress damage was also determined by the level of urinary 8-OHdG. Lycopene treatment significantly decreased urinary 8-OHdG levels in a dose-dependent manner (P<0.001), with the highest lycopene dose showing the greatest decrease (P<0.001).

Biochemical Markers of Bone Turnover:

Biochemical BTMs provided insight into the systemic skeletal response to lycopene treatment. Consistent with the effects of OVX, levels of two bone formation markers (BFMs), s-OC and s-P1NP, were significantly increased in the OVX control group compared with SHAM group [means at week 12: s-OC (ng/ml) 33.93±3.36 in OVX vs. 24.41±3.55 in SHAM and s-P1NP (ng/ml) 10.51±1.01 in OVX vs. 6.63±0.41 in SHAM (P<0.001 in each case)]. Treatment of OVX rats with lycopene at 30 or 45 mg/kg body weight per day resulted in significant decreases in s-OC and s-PINP levels (P<0.001 in each case) compared with the OVX control group at weeks 8 and 12 (FIG. 6A, 1B). ALN treatment significantly decreased s-OC and s-PINP levels at week 12 compared with the OVX control group (P<0.001 in each case) (FIG. 6A, B). Consistent with the effect of OVX, significant increases were observed in levels of bone resorption markers (BRMs) s-CTX and u-DPD in the OVX control animals compared with SHAM controls at 8 and 12 weeks of treatment (P<0.001; in each case). Treatment of OVX groups with lycopene (30 and 45 mg/kg body weight per day) significantly decreased s-CTX and u-DPD levels compared to the OVX control group (P<0.001 in each case). Treatment with ALN prevented the OVX-induced increases in s-CTX and u-DPD levels over those seen in the SHAM group (P<0.001 in each case) (FIG. 6 C, D).

In Vivo DXA Densitometry of Lumbar Spine and Humerus:

To establish whether alterations in bone density occurred in response to treatment, an in vivo DXA densitometry measurements were carried out. The OVX control group showed significant decreases in BMC and BMD values in both the lumbar spine (0.48-fold for BMC and 1.9-fold for BMD; P<0.001 in each case) (FIG. 7 A, B) and humerus (1.7-fold for BMC and 1.45-fold for BMD; P<0.001 in each case) (FIG. 7 C, D) as compared with corresponding SHAM controls at week 12 of treatment. Lycopene treatment significantly prevented OVX-induced bone loss with marked increases in both BMC and BMD in the lumbar spine (P<0.001) (FIG. 2A, B) and humerus (P<0.05) (FIG. 7 C, D) compared with the OVX control group. As expected, ALN prevented OVX-induced bone loss, with significantly higher BMC and BMD values than OVX controls for both lumbar spine (P<0.001) and humerus (P<0.01), comparable to, or higher than, the SHAM control group (FIG. 7 A, B, C, D).

In Vivo pQCT Densitometry of Tibia Metaphysis:

In order to characterize the effects of lycopene treatment on trabecular and cortical bone compartments, in vivo pQCT densitometry measurements were observed on proximal tibia metaphysis. After 12 weeks of treatment, the OVX control group exhibited significantly lower values compared to SHAM controls in proximal tibia trabecular BMD (−41.6±1.2 vs. −9.2±1.1%, P<0.05), cortical/subcortical BMD (decreased 5-fold, P<0.001), and total BMD (−12.1±0.3 vs. −1.06±0.12%, P<0.001) (FIG. 8 A, B, C, respectively). Lycopene treatment significantly prevented OVX-induced bone loss for both total and trabecular BMD in the proximal tibia (P<0.001). ALN prevented OVX-induced bone loss, with significant differences in total slice BMD and BMC (P<0.001 in each case) compared with the OVX control group. A marked differences in cortical/sub-cortical BMD and trabecular BMD values (P<0.001 in each case) for the ALN-treated group versus the OVX group (FIG. 8 A, B, C) was observed.

Ex Vivo pQCT Densitometry of Lumbar Spine and Femur Diaphysis and Bone Strength:

Using ex vivo pQCT densitometry, various biomechanical parameters were determined for the lumbar spine, including peak load, apparent strength, yield load, yield stress, stiffness, modulus, AUC, and toughness, following the 12-week intervention (FIG. 9 A, B, C). Consistent with the effect of OVX, mean values for biomechanical parameters in the lumbar spine of the OVX control group were lower than the SHAM control group at the end of the 12-week period. These effects were concurrent with changes in BMC and BMD values measured by pQCT (P<0.001). Lycopene treatment, particularly at doses of 30 and 45 mg/kg body weight per day, significantly rescued OVX-induced bone loss and improved biomechanical parameters (P<0.05). ALN treatment significantly increased bone strength parameters at the lumbar spine (P<0.05 for all). These increases were associated with statistically significant increases in BMC and BMD values (P<0.001 for both). The effects of interventions on bone strength parameters (peak load, ultimate stress, stiffness, modulus, AUC, and toughness) in the femur (FIG. 9 D, E, F) were determined. Ex vivo pQCT analysis was performed at the expected fracture site, the femur diaphysis. There were significant decreases in BMD and bone strength in response to OVX vs. the SHAM control group at week 12 of treatment. Treatment with lycopene prevented the negative effects of OVX on bone strength parameters in the femur diaphysis, restoring values comparable to the SHAM control group.

With respect to cortical bone geometry, cortical thickness significantly decreased in the OVX group vs. the SHAM group. This decrease was associated with a small but marked decrease in periosteal circumference (P<0.05), but not with changes in endosteal circumference. Lycopene treatment (particularly 45 mg/kg body weight per day) prevented the decrease in cortical thickness and even induced higher values over the SHAM group. This increase was accompanied by significant decreases in endosteal circumference. Alendronate prevented the OVX-induced decrease in cortical thickness and periosteal circumference.

Ex Vivo μCT Analysis of the Tibial Metaphysis and Femur Diaphysis:

In order to further characterize the effects of treatment on the trabecular and cortical bone compartments, the tibial metaphysis and femoral diaphysis using ex vivo μCT analysis were evaluated. The results for trabecular (tibia metaphysis) and cortical (femur) bone for various parameters are presented in Table 4. As expected, compared with the SHAM group, OVX-induced trabecular bone loss was evident, with significant decreases in relative bone volume (BV/TV, 54.5%), trabecular number (Tb.N, 33.3%), and trabecular thickness (Tb.Th, 19.3%), and with significant corresponding increases in trabecular separation (Tb.Sp, 26.7%) (P<0.0001 in each case). Lycopene treatment, restored trabecular bone in OVX groups in a dose-related manner, with 45 mg/kg body weight per day showing the highest effect. Table 4 illustrates significant increases in BV/TV (123.9%), Tb.N (52.8%), and Tb.Th (78.4%), with a corresponding significant decrease in Tb.Sp (46.8%), as compared with the OVX group (P<0.001 in each case). Similarly, treatment with ALN prevented OVX-induced trabecular bone loss comparably with 45 mg/kg body weight daily lycopene treatment; mean values for BV/TV (128.9%) and Tb.N (by 25.8%) significantly increased, and Tb.Sp significantly decreased (37.3%) compared with the OVX control group (P<0.001 for all). Interestingly, neither OVX, nor lycopene or ALN treatment had significant effects on the relative bone volume (BV/TV) of the femur diaphysis. However, ALN treatment and 30 and 45 mg/kg body weight per day lycopene treatment improved femoral cortical values for Ct.Th and Ct.Po as compared with the SHAM and OVX groups (P<0.001 in each case), but as with BV/TV (%) the improvement did not reach statistical significance.

Dynamic Bone Histomorphometric Analysis of the Tibial Metaphysis and Diaphysis:

Data showed the results of dynamic histomorphometric analyses for trabecular and cortical bone parameters in the tibia. The OVX control group exhibited marked bone loss in the tibial metaphysis vs. the SHAM control, with significant decreases in BV/TV (45.3%, P<0.001) and Tb.N (36.8%, P<0.001). OVX was associated with significant increases in osteoblast surface (14.2-fold, P<0.0001) and fat tissue volume (3.2-fold, P<0.0001). Mineralizing surface (P<0.0001), and bone formation rates (BFR/BS and BFR/BV, P<0.0001) were also increased in the OVX group vs. the SHAM group. Finally, the osteoclast-derived variables, Oc.S/BS (29.3%) and N.Oc/BS (42.7%), also increased following OVX (P<0.001 for both). Treatment with lycopene prevented OVX-induced trabecular bone loss in the tibial metaphysis, with significant increases in BV/TV (range: 27.1-92.2%) and Tb.N (range: 9.2-72.9%) compared with the OVX control group. Treatment with 45 mg/kg body weight per day lycopene showed the greatest effect. Lycopene treatment prevented OVX-induced increases in bone formation parameters measuring osteoblast surface (Ob.S/BS %), mineralizing surface (MS/BS, %), BFR/BS, and BFR/BV. Further, lycopene treatment decreased OVX-induced bone resorption as indicated by significant decreases in osteoclast surface (Oc.S/BS, %) and osteoclast number (N.Oc/BS, %) ($P<0.001$ for both). Such changes were either comparable to or even lower than levels for the SHAM group, demonstrating that lycopene treatment completely reversed OVX-bone changes and increased bone turnover. Similar responses in the ALN group was observed. The cortical bone indices on the periosteal and endocortical surfaces were assessed. OVX significantly affected many of the structural parameters measured in the tibial diaphysis. Changes included increased labeled surface and bone formation rate at the periosteal compartment as demonstrated by periosteal labeled surface (Ps.L.Pm/Ps.Pm, %) (2.7-fold), periosteal MAR (Ps.MAR) (41.2%), and periosteal BFR (Ps.BFR/BS) (2.7-fold) ($P<0.001$ for all). Interestingly, increased endocortical labeled surface (Ec.L.Pm/Ec.Pm, %) (1.7-fold), mineral apposition (77%), and BFR (5.1-fold) were evident. In addition, at the endocortical eroded surface, an indicator of bone resorption was also increased (1.14-fold) as a consequence of OVX ($P<0.001$ for all). Lycopene treatment greater than 15 mg/kg body weight per day completely prevented OVX-related increases in endocortical bone turnover formation; Ec.L.Pm/Ec.Pm, Ec MAR, and Ec.BFR/BS were comparable to the SHAM group. Lycopene treatment positively affected bone dynamics on the periosteal surface (except at 45 mg/kg body weight per day). For the most part, the ALN group also prevented OVX-induced effects.

Osteoblast and Osteoclast Differentiation, Activity, Apoptosis, and Anti-Oxidative Stress Enzymes:

The RNAs encoding proteins associated with osteoclast differentiation and activity using total RNA prepared from bone marrow aspirates were measured. As expected, transcription of mRNA encoding the osteoclastogenesis regulator, nuclear factor of activator T-cells cytoplasmic 1 (Nfatc1), was up-regulated in response to OVX (FIG. 10 A). Lycopene treatment suppressed the OVX-induced increase in Nfatc1 and restored the relative level of expression to that of the SHAM group (FIG. 10A). Similarly, OVX increased the expression of both OPG and RANKL compared to the SHAM control group. Binding of RANKL to its cognate receptor, RANK, activates osteoclasts. OPG, a soluble member of the tumor necrosis receptor super-family, acts as a naturally occurring decoy receptor that competes with RANK for binding of RANKL. The balance of these two molecules plays a critical role in the control of osteoclastogenesis. All three doses of lycopene treatment down-regulated RANKL, while higher doses of lycopene decreased OPG. Accordingly, the concentration ratio of RANKL/OPG was decreased by as much as 18.9% and 38.3% for lycopene doses of 30 and 45 mg/kg body weight per day, respectively ($P<0.05$) (FIG. 10 E).

To examine changes in osteoblast activity, RNA from flushed femurs to assess gene expression. Col1a1 gene expression was increased by OVX and remained elevated in response to lycopene treatment was used. In addition, a statistically significant changes at the end of the study in both Ocn and ALP due to OVX or lycopene treatment, suggesting transcriptional regulation of osteoblast activity and mineralization (FIG. 10 C, D) were observed. Another plausible mechanism by which lycopene treatment may have affected bone formation and resorption in the OVX model was by regulating osteoblast and/or osteoclast apoptosis. Bcl-2 homologous antagonist/killer 1 (Bak1) promotes apoptosis by forming channels in the outer mitochondrial membrane. In the osteoclast- and osteoclast precursor-rich bone marrow, Bak1 mRNA abundance was up-regulated by lycopene treatment as compared to the OVX control group (FIG. 10 G, H). In flushed femurs, gene expression of the essential proteases involved in apoptosis, Casp 9 and Casp 3, was down-regulated in response to OVX, and did not change in response to lycopene treatment (FIG. 10 I, J).

Finally, to investigate the changes in GPx-1, CAT and SOD activities specifically in bone, RNA from flushed femurs to assess GPX-1, CAT and SOD gene expression. GPX-1, CAT and SOD expressions were significantly decreased by OVX, and lycopene treatment increased the relative expression of all anti-oxidative stress enzymes to a level higher than that of the SHAM group (FIG. 10 F) were used.

The efficacy of lycopene for treatment of postmenopausal physiological changes was investigated. An ovariectomized rat model to mimic the loss of estrogen associated with menopause was utilized. As expected the mean uterine weight in OVX rats was significantly lower than in the SHAM group ($P<0.001$). Lycopene supplementation increased uterine weight in a dose-dependent way ($P<0.01$), but uterine weight was still lower in all lycopene-treated OVX groups than the SHAM group ($P<0.001$). Moreover, mean body weights were greater in the OVX control group than in the SHAM group ($P<0.001$). Lycopene treatment prevented OVX-induced body weight gain and fat accumulation (as indicated by body composition analysis). Interestingly, lycopene treatment significantly increased serum $E_2$ levels in a dose-dependent fashion and attenuated the elevated serum FSH and LH levels resulting from the removal of $E_2$ in OVX rats, indicating that lycopene has a beneficial role in regulating hypothalamic-pituitary function. Further studies are needed to explore the underlying mechanisms for these observations.

The bulk of the study focused on bone changes associated with estrogen loss. Osteoporosis is an inflammatory metabolic disorder characterized by loss of bone mass and strength resulting in fragility fractures. Deterioration of the trabecular architecture in particular has been implicated in diminished bone strength and increased prevalence of fractures. Accordingly, BTMs, BMD, trabecular and cortical structures, and bone biomechanical parameters as indicators of osteoporosis in an OVX rat model were selected. A battery of investigative modalities to examine bone response to lycopene treatment were used. In addition, alterations in regulators of osteoblast and osteoclast differentiation and activity at the tissue level together with oxidative stress indicators during lycopene treatment were examined.

Bone densitometry data confirmed that lycopene is osteoprotective and possesses bone-sparing effects, at least in the OVX rat model. Lycopene treatment prevented the loss of trabecular bone in tibia, vertebrae, and femurs. Alterations in trabecular bone in response to lycopene treatment coincided with improved BTM levels and biomechanical properties, including bone strength and stiffness. Such biomechanical and structural improvements suggest that lycopene treatment results in enhanced bone quality. The decrease in BMD with the concurrent deterioration of bone microarchitecture induced by ovariectomy is closely associated with a high rate of bone remodeling and an imbalance between bone formation and resorption. In the present study, lycopene treatment resulted into significant decreases in BRM levels (both s-CTX and u-DPD) compared with the OVX control group. Such changes were accompanied by significant decreases in BFMs (both s-OC and s-P1NP). Consistent with these changes, were observed marked effects of lycopene treatment in BFR, MAR, and number of osteoblasts at 12 weeks of treatment, as determined by histomorphometric analysis. In addition, histomorphometric findings (Oc.S/BS or N.Oc/BS) showed increase in bone resorption suggested by changes in BRM levels.

The loss of bone mass caused by OVX, measured by in vivo and/or ex vivo DXA, pQCT, μCT, and histomorphometry analysis, was partially or completely prevented by lycopene treatment, particularly at higher doses. These findings suggest that lycopene treatment of 30 or more mg/kg body weight per day has the capacity to decrease OVX-induced bone loss by suppressing bone resorption, the major contributor to bone loss in ovarian hormone deficiency. Importantly, lycopene also acts to uncouple catabolic and anabolic activities in bone and appears to shift the balance slightly towards osteogenic activity, increasing BMD. By comparison, ALN therapy in OVX rats increased bone mass and strength; such effects were mediated by decreased bone resorption and formation, as demonstrated by changes in osteoclasts, osteoblast and label-derived histomorphometric variables, and systemic BTMs.

Histomorphometric analysis demonstrated that OVX decreased bone volume fraction and trabecular number and increased trabecular separation, mineralizing surface, and formation rate of trabecular bone. In addition, OVX increased periosteal and endocortical bone turnover of cortical bone. Lycopene treatment partially or completely prevented the OVX-induced micro=architectural deteriorations in trabecular bone, with lesser effects in cortical bone. Lycopene treatment was effective in suppressing the increase in bone porosity in rat femurs caused by OVX, indicating that lycopene treatment (particularly 45 mg/kg body weight per day) thickens and strengthens cortical bone. The bone-protective effects of lycopene, including osteogenesis promotion, trabecular bone thickening, and trabecular connectivity strengthening, are consistent with the effects of lycopene treatment on BRM and BFM levels and increases in bone mass.

Lycopene treatment was effective at increasing the apparent strength, toughness, and Young's modulus of lumbar vertebrae, as well as the ultimate stress, toughness, and modulus of the whole femur. The lumbar vertebrae and femurs of rats receiving lycopene, particularly doses of 30 or 45 mg/kg body weight per day, resisted deformation much better than even the SHAM group. This indicates that lycopene treatment had a great effect on biomechanical properties and maintained bone strength to protect against the deleterious effects of ovariectomy.

In general, the histomorphometric analysis was concordant with the bone densitometry (DXA, pQCT, and μCT) and bone strength findings. Lycopene treatment and ALN treatment significantly ameliorated changes in the trabecular structure, though the time of onset of these effects and their profile may not be completely uniform among treated individuals.

High ROS production exacerbates aging-induced and estrogen deficiency-induced bone loss by causing deterioration of cellular enzymes like GPx. Thus, it is important to assess whether lycopene treatment could improve cellular antioxidant enzyme levels and decrease oxidative damage, and whether such an impact of lycopene treatment would correlate with the increased bone mass. A lower activity of plasma GPx, CAT and SOD levels and higher urinary 8-OHdG in the OVX control group as compared to the SHAM group was shown. After lycopene treatment, plasma GPx, CAT and SOD activities increased and urinary 8-OHdG levels significantly decreased. The anti-oxidative defense systems, including GPx, CAT and SOD, investigated herein might prevent oxidative damage in the bone during bone remodeling. The osteoprotective effects of lycopene may be partly due to its antioxidant capacity. This hypothesis was further supported by the observed up-regulation of GPX-1, CAT and SOD gene expression in response to lycopene treatment in bone marrow cells of OVX rats.

Due to the novelty of Nanoformulated lycopene exhibiting osteoprotective activities associated with decreased resorption and enhanced formation of bone, the relative mRNA abundance of key genes involved in the regulation of osteoblast and osteoclast differentiation and activity were studied. Here, it is reported for the first time that in bone marrow cells isolated from OVX rats, lycopene treatment decreased osteoclastogenesis through the down-regulation of Nfatc1 gene expression (the master regulator of osteoclastogenesis), while simultaneously up-regulating osteoblast activity by enhancing Alp, Colla1 and Ocn mRNA. This confirms the dual anti-resorptive and anabolic actions of lycopene and represents an uncoupling of bone turnover in favor of accrual of new bone tissue. It is also reported for the first time that RANKL and OPG were both down-regulated in OVX lycopene treated rats at 12 weeks, indicating that the influence of lycopene on bone in response to OVX is partly mediated by the RANK-signaling pathway. Lycopene treatment decreased the formation of ROS and the concentration ratio of RANKL/OPG, which might explain its suppressive effect on OVX-induced osteoclastogenesis.

Also explored was the concept that lycopene could alter osteoblast and/or osteoclast populations via apoptosis. The results show for the first time that OVX decreased Bak1 gene expression in the bone marrow compared to SHAM, indicating that estrogen deficiency promotes osteoclastogenesis by up-regulating Nfatc1 and also suppresses mitochondria-mediated apoptosis. A novel action of lycopene prevented the OVX-induced decrease in Bak1 gene expression, suggesting that lycopene treatment may not only suppress the formation of osteoclasts, but may also prohibit the OVX-induced decrease in apoptosis. In addition, the observations related to the expression of Casp3 and Casp9 mRNA in the OVX animals are consistent with a decrease in osteoblast apoptosis. Taken together, these results suggest a possible difference in transcriptional regulation of apoptosis in bone marrow and mineralized bone that warrants further investigation.

In addition to the mechanisms suggested above for the of action of lycopene, other possible mechanisms explaining the lycopene bone-protective effect include its anti-inflammatory action, and its potential to induce direct intracellular gap junction communication, redox-sensitive signaling pathways, and to regulate cell proliferation and differentiation. Accordingly, it is possible that lycopene acts directly on bone metabolism, as well as restoring oxidative stress pathways in metabolic bone diseases including conditions of postmenopausal osteoporosis. Lycopene stands as a promising safe, effective, and natural treatment for postmenopausal osteoporosis, and its potential benefits should be vigorously investigated.

In conclusion, lycopene treatment for 12 weeks demonstrated bone-protective effects similar to ALN, improving the biomechanical properties of bone and inhibiting bone resorption in OVX rats. Such effects appear to be primarily due to decreased bone turnover, as indicated by changes in BTMs and other microarchitecture parameters. Moreover, these structural changes coincided with local up-regulation of indicators of osteoblast activity and the down-regulation of osteoclastogenesis. Such changes in mediators of bone metabolism occurred in conjunction with enhanced systemic GPx, CAT and SOD activities and decreased urinary 8-OHdG excretion. A limitation of the present study is that most of the data presented here provide evidence for transcriptional regulation of osteogenesis and it remains to be seen whether lycopene will affect osteoblastogenesis and/or osteoclastogenesis on a translational level. Further studies in humans are needed to confirm the observations and the usefulness of lycopene as an osteoprotective agent in humans. Nevertheless, the results may provide the opportunity for the development of a novel intervention for aging-related bone loss and for osteoporosis prevention.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A nano-composition, comprising:
nanoparticles, each nanoparticle comprising a shell encapsulating lycopene, said shell comprising oligomerized (−)-epigallocatechin-3-O-gallate (OEGCG) electrostatically bonded to chitosan.

2. The nano-composition of claim 1, wherein the shell is coated with a targeting moiety configured to target the nanoparticle to a liver of a human being to which the nanoparticles are administered.

3. The nano-composition of claim 2, wherein the targeting moiety is Glycyrrhizin.

4. The nano-composition of claim 1, wherein the shell further comprises the chitosan covalently bonded to a carboxyl group of each polymer of one or more polymers, wherein the one or more polymers are selected from the group consisting of hyaluronic acid, Poly(Lactide-co-Glycolide) (PLGA), one or more fatty acids, and combinations thereof, and wherein the one or more fatty acids are selected from the group consisting of oleic acid, myristic acid, docosahexaenoic acid (DHA), eicosapentaenoic acid (EPA), and combinations thereof.

5. The nano-composition of claim 4, wherein the one or more polymers comprise the hyaluronic acid.

6. The nano-composition of claim 4, wherein the one or more polymers comprise the PLGA.

7. The nano-composition of claim 4, wherein the one or more polymers comprise the one or more fatty acids.

8. The nano-composition of claim 1, wherein the shell encapsulates one or more bioactive compounds comprising polyphenols.

9. The nano-composition of claim 1, wherein the chitosan has a molecular weight in a range of 5,000 to 100,000 Daltons.

10. The nano-composition of claim 1, wherein each nanoparticle has a linear size in a range of 100 to 500 nm.

11. The nano-composition of claim 1, wherein each nanoparticle has a positive zeta potential in a range of +10 to +30 mv.

12. A method of forming the nanoparticles in the nano-composition of claim 1, said method comprising:
mixing lycopene in olive oil with docosahexaenoic acid (DHA) and/or eicosapentaenoic acid (EPA) in a presence of Cremopher EL and Tween 20, wherein the formed nanoparticles are solid lipid nanoparticles.

13. The method of claim 12, said method further comprising:
lyophilizing the nanoparticles; and
prior to said lyophilizing the nanoparticles, adding mannitol or sucrose as a cryoprotectant to the nanoparticles.

14. A method of using the nano-composition of claim 1, said method comprising:
administering the nano-composition to a human being.

15. The method of claim 14, wherein said administering the nano-composition to the human being comprises administering the nano-composition orally, topically, or by injection.

* * * * *